(12) United States Patent
Shin et al.

(10) Patent No.: US 7,723,917 B2
(45) Date of Patent: May 25, 2010

(54) METHOD OF DE NOVO SEQUENCING OF PEPTIDE USING THE MALDI MASS SPECTROMETRY, METHOD AND APPARATUS FOR PREPARING SAMPLE FOR MALDI MASS SPECTROMETRY

(75) Inventors: Seung-Koo Shin, Pohang (KR); Kyung-Hwan Jeong, Pohang (KR); Hye-Joo Yoon, Pohang (KR); Min-Soo Suh, Gyeongsanbuk-do (KR); Jong-Cheol Seo, Pohang (KR)

(73) Assignees: POSTECH Foundation, Pohang (KR); Posco, Pohang (KR); Postech Academy-Industry Foundation, Pohang (KR)

( * ) Notice: Subject to any disclaimer, the term of this patent is extended or adjusted under 35 U.S.C. 154(b) by 203 days.

(21) Appl. No.: 11/817,979

(22) PCT Filed: Mar. 8, 2006

(86) PCT No.: PCT/KR2006/000821

§ 371 (c)(1),
(2), (4) Date: Oct. 1, 2007

(87) PCT Pub. No.: WO2006/096012

PCT Pub. Date: Sep. 14, 2006

(65) Prior Publication Data

US 2008/0138845 A1 Jun. 12, 2008

Related U.S. Application Data

(60) Provisional application No. 60/660,180, filed on Mar. 8, 2005.

(51) Int. Cl.
*H01J 17/26* (2006.01)
(52) U.S. Cl. .................................................. 313/564
(58) Field of Classification Search ......................... None
See application file for complete search history.

(56) References Cited

FOREIGN PATENT DOCUMENTS

| EP | 1 186 888 | 3/2002 |
|---|---|---|
| WO | 9957318 | 11/1999 |
| WO | 02/083923 | 10/2002 |

OTHER PUBLICATIONS

Kalume et al. "Structure determination of two conotoxins from Conus textile by a combination of matrix-assisted laser desorption/ionization time-of-flight and electrospray ionization mass spectrometry and biochemical methods", J of Mass Spec., 2000, 35:145-156.*
Pappin D J C, Peptide Mass Fingerprinting Using MALDI-TOF Mass Spectrometry, Methods Mol Biol, 64, 1997, 165-173.
Kim T-Y et al.,Effect of Tryptic Peptide Esterification in MALDI Mass Spectrometry, Anal Chem, 77(13), 2005, 4185-4193.
Brancia FL, et al, Guanidino Labeling Derivatization Strategy for Global Characterization of Peptide Mixtures by Liquid Chromatography Matrix-Assisted Laser Desorption/Ionization Mass Spectrometry, In: Analytical Chemistry, vol. 76 (10), May 15, 2004, pp. 2748-2755.
Keough T, et al, Derivatization procedures to facilitate de novo sequencing of lysine-terminated tryptic peptides using postsource decay matrix-assisted laser desorption/ionization mass spectrometry. In: Rapid Commun. Mass Spectrom. 14 (24), Online Nov. 23, 2000, pp. 2348-2356.
Lee YH, et al, Highly informative proteome analysis by combining improved N-terminal sulfonation for de novo peptide sequencing and online capillary reverse-phase liquid chromatography/tandem mass spectrometry, In: Protemics, vol. 4 (6), Jun. 2004, pp. 1684-1694.
Huang Z-H., et al, Protein Sequencing by Matrix-Assisted Laser Desorption Ionization—Postsource Decay—Mass Spectrometry Analysis of the N-Tris(2,4,6-trimethoxyphenyl)phosphine-Acetylated Tryptic Digests. In: Analytical Biochemistry, vol. 268(2), Mar. 15, 1999, pp. 305-317.
Seung Koo Shin: "None" Internet Article, [Online] Apr. 22, 2004,-Oct. 22, 2004 pp. 1-6, XP002540421 Retrieved from the Internet: URL:http://hemos.postech. ac.kr/erpweb/ps_res10009002.php?id=00020360&lang-EN> [retrieved on Aug. 6, 2009] Paragraph "Invited Talk or Presentation": Item 27 "Focused Electrospray for LC MALDI Coupling" and Item 33 "Development of an automated LC-MALDI sample deposition interface using electrospray".
Foret F et al: "Liquid phase interfacing and miniaturization in matrix-assisted laser desorption/ionization mass spectrometry" Proteomics, vol. 2, No. 4, Apr. 2002, pp. 360-372, XP002540422.
Ericson C et al: "An automated noncontact deposition interface for liquid chromatogrpahy matrix-assisted laser desorption/ionization mass spectrometry." Anal Chem, vol. 75, No. 10, May 15, 2003, pp. 2309-2315, XP002540423.

* cited by examiner

*Primary Examiner*—Karen Cochrane Carlson
*Assistant Examiner*—Bin Shen

(57) ABSTRACT

The present invention relates to a method of peptide sequencing by MALDI (matrix-assisted laser desorption ionization) tandem mass spectrometry, which comprises the steps of chemically modifying a sample peptide with at least one chemical modification method selected from the group consisting of guanidination and esterification in order to change the ionization status of the peptide and performing mass spectrometry using a MALDI tandem mass spectrometer and programmed MALDI tandem mass spectrometry. The peptide sequencing method of the present invention is advantageous in that detection sensitivity of the peptide improves significantly and various daughter ions are detected uniformly, thereby enabling perfect de novo sequencing with tandem mass spectrometry only, without database search.

10 Claims, 18 Drawing Sheets

METHOD OF DE NOVO SEQUENCING OF PEPTIDE USING THE MALDI MASS SPECTROMETRY, METHOD AND APPARATUS FOR PREPARING SAMPLE FOR MALDI MASS SPECTROMETRY

BACKGROUND OF THE INVENTION (a) Field of the Invention

The present invention relates to a method of peptide sequencing by MALDI (matrix-assisted laser desorption ionization) tandem mass spectrometry in which an ionization status and chemical property of peptide are modified by at least one chemical modification selected from the group consisting of guanidination and esterification.

The present invention also relates to a method for preparing a sample for MALDI mass spectrometry including coating charged particles formed by electrospraying a sample solution under atmospheric pressure on a MALDI substrate using an ion-optical focusing instrument and an apparatus for electrospraying and focusing for the same.

(b) Description of the Related Art

At present, the most frequently used technique for identifying and characterizing proteins is based on mass spectrometry. However, the current technique is limited in detection sensitivity, making it applicable only to large volume of protein samples or readily ionized samples. Further, the sequencing requires a long time and only a limited number of proteins can be analyzed. Thus, researches are underway to find techniques capable of analyzing a large volume of samples in a short time and of improving detection sensitivity.

Tandem mass spectrometry is used in peptide sequencing of peptides. A peptide to be sequenced is selectively fragmented and the mass of the resultant daughter ions is measured to obtain the amino acid sequence of the peptide. The tandem mass spectrometry data are utilized to identify the particular protein by comparison with a gene sequence database. However, it is known that the reliability of this process is only 10 to 35%.

Such low reliability results from cleavage at a particular amino acid residue of a peptide or wrong daughter ion labelling caused by internal fragmentation. According to a recent research, monovalent (+1) ions mainly generated by matrix-assisted laser desorption ionization (MALDI) experience less internal fragmentation during tandem mass spectrometry than multivalent (+n, n≧2) ions mainly generated by electrospray ionization (ESI).

However, monovalent ions show a large difference in detection sensitivity depending on the amino acid composition of the particular peptide and cleavage tends to be concentrated around a specific amino acid residue, giving non-uniform daughter ion distribution. Despite these problems, MALDI is better suited for protein research, in which only a small amount of a sample is available, than ESI because it requires only a small volume of a sample, is not significantly affected by salts, and is convenient in spectrum analysis. Thus, a lot of attempts have been made in order to solve the problem in sequencing monovalent peptide ions generated by MALDI.

MALDI-MS is a cutting-edge soft ionization technique used in mass spectrometry, allowing, among other things, analysis of biomolecules (including proteins) and polymers. In contrast with ESI-MS, MALDI-MS is less affected by contamination of the sample from buffer solution, salt, bleaching agent, etc., requires a smaller sample, enables quick analysis, and makes it possible to perform a variety of re-analysis, including peptide sequencing, until the sample is depleted. However, because MALDI-MS requires a solid sample, it is not readily compatible with separation techniques treating liquid samples, in comparison with ESI-MS. To overcome this problem, continuous-flow probes or aerosol interfaces have been used to couple LC (liquid chromatography) with MALDI-MS and enable on-line MALDI-MS measurement. However, they have not satisfied the requirements in resolution, accuracy, and detection sensitivity needed for proteomics research. Although on-line MALDI-MS using moving wheels or moving balls in a vacuum container showed some improvement in resolution and detection sensitivity, it was restricted to a flow rate of nanoliters per minute and had no practicability or applicability.

Researches have been made on off-line MALDI-MS, in which, differently from on-line MALDI-MS, effluent from LC or capillary LC is fractionally collected to prepare samples adequate for MALDI-MS. The early technique used for off-line MALDI-MS analysis was fractionally collecting effluent using micro-vials or a 96-well micro-titer plate, concentrating each fraction by, for example, SpeedVac, mixing them with a matrix, and loading on a MALDI plate. This process was problematic in that a long time is required and automation is difficult. In addition, loss of the sample during concentration and sample-matrix preparation was a fatal problem. To solve these problems, several groups have developed automation methods for loading LC effluent directly on a MALDI plate as a spot or a track using such techniques as micro-dispenser piezoelectric flow, blotting, vacuum-assisted deposition, electric field-driven droplet deposition, heated nebulization, heated droplet delivery. However, these methods are adequate only for nanoflow or very slow flow. Besides, as heat or an impact is directly applied to the sample, it may be modified physically or chemically. Also, loss of sample is inevitable. Particularly, all the techniques developed thus far provide too large spots, which is the typical problem of MALDI sample preparation, resulting in dearth of sample per unit area and poor in-spot homogeneity or spot-to-spot homogeneity. As a result, a lot of time has to be spent to find out the "sweet spot", or the sample/matrix crystal. Therefore, samples with smaller quantity or lower abundance tend not to be detected.

Also, because the sample/matrix crystal is too large, a lot of matrix ions are generated during laser desorption ionization, resulting in noise during the sample detection. With the conventional methods, signals of about 800 Da or less are not detected in general, because they are screened by the matrix ions.

SUMMARY OF THE INVENTION

The present invention was made to overcome the aforementioned problems of the de novo sequencing technique using MALDI mass spectrometry, that is, the wide variation of detection sensitivity depending on the amino acid composition of a peptide and the non-uniform daughter ion distribution due to concentrated decomposition at a particular amino acid residue. Accordingly, it is an object of the present invention to provide a method for peptide sequencing in which detection sensitivity of a peptide is improved and daughter ion distribution is made uniform by chemical modification.

It is another object of the present invention to solve the problem of the conventional LC-MALDI MS coupling technique and to lower the sample detection limit and reduce noises caused by ions generated from the matrix using an electrospray collection apparatus to coat a highly uniform and concentrated sample with smaller sample/matrix crystal size on a MALDI plate, thereby enabling uniform mass detection of a sample in every region, without needing a "sweet spot", with reduced shot-to-shot fluctuation.

DETAILED DESCRIPTION OF THE PREFERRED EMBODIMENTS

In order to obtain the affore-mentioned objects, the present invention provides, as an embodiment, a method of amino acid sequencing by MALDI tandem mass spectrometry that includes the steps of:

chemically modifying a sample peptide by at least one chemical modification method selected from the group consisting of guanidination and esterification;

performing mass spectrometry using a MALDI tandem mass spectrometer; and a programmed de novo sequencing.

The present invention may further include the step of preparing the sample peptide through treatment of a protein with a protease, prior to the chemical modification.

Figure 1:
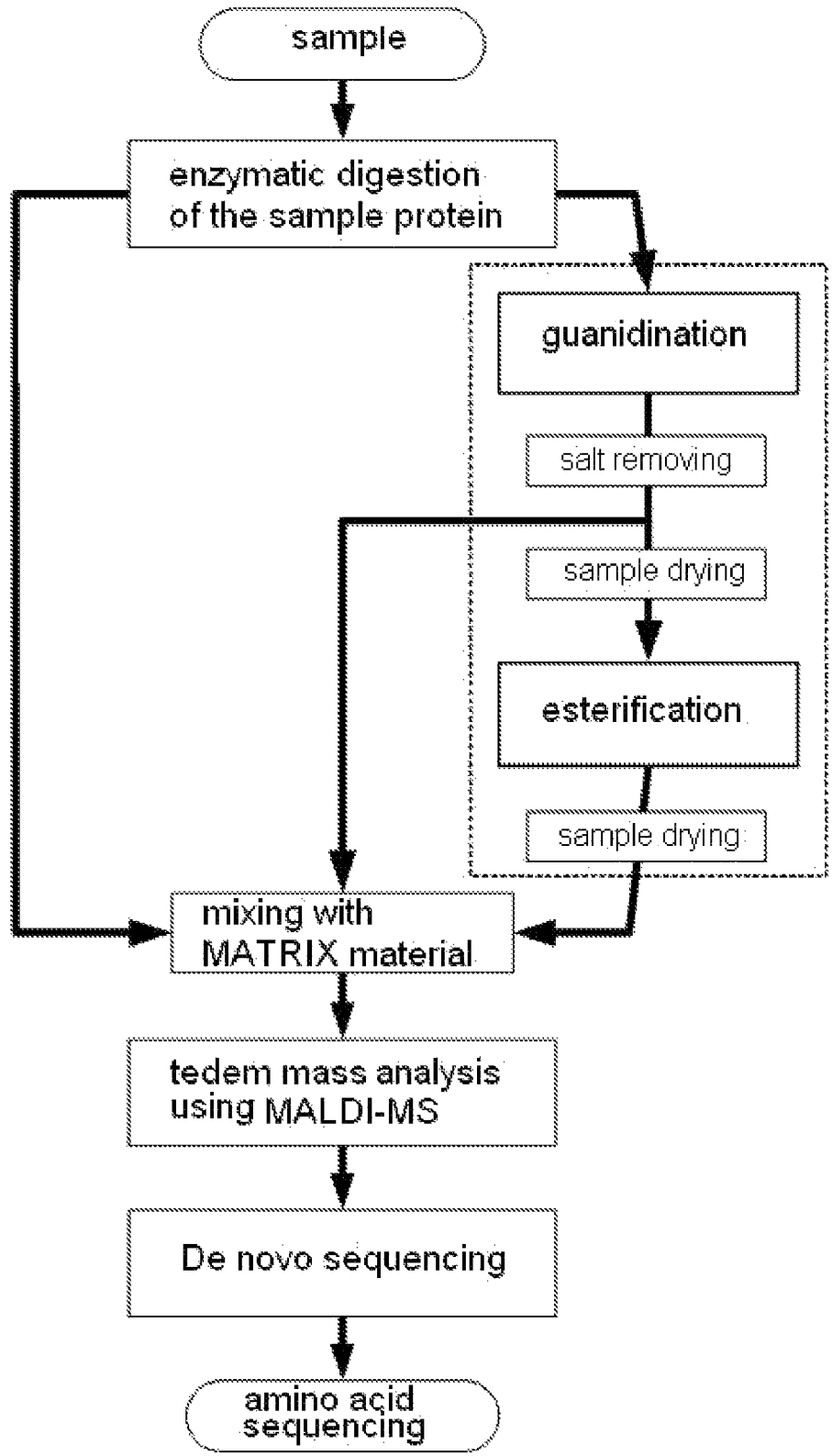
FIG. 1 is a block diagram illustrating the entire process of peptide sequencing in accordance with the present invention.

Hereafter is given a more detailed description of the present invention referring to FIG. 1.

(a) Enzymatic Cleavage of a Protein of Interest

In the case that the sample peptide is prepared by treating a protein with a protease, prior to the chemical modification, the protease used in the enzymatic cleavage may be one commonly used in amino acid sequencing by the conventional MALDI tandem mass spectrometry. Preferably, a protease that produces a Lys or Arg C-terminus, more preferably, trypsin, lysine C (LysC), or a mixture thereof, may be used. Also, the present invention may be effectively applied to peptides obtained by enzymatic cleavage with trypsin or lysine C and other protease.

Proteins to which the method of the present invention can be applied are intended to include peptides, polypeptides, and proteins.

(b) Chemical Modification

The C-terminus of an amino acid or a protein can be chemically modified by at least one chemical modification selected from the group consisting of guanidination and esterification.

De novo sequencing refers to an amino acid sequencing technique based on a mass of daughter ions only, without regard to other data. De novo peptide sequencing is indispensable because data of all proteins are not listed in the database and a large number of proteins are altered after transcription. For successful de novo sequencing of monovalent ions generated by MALDI, improvement of detection sensitivity, which may be poor depending on the amino acid composition, and reduction of selective cleavage at a particular amino acid residue are important. Thus, in the present invention, tryptic peptides are chemically modified in order to improve detection sensitivity of the tryptic peptide containing lysine at the carboxy-terminus and reduce selective cleavage at a particular amino acid residue during the tandem mass spectrometry, thereby offering a uniform daughter ion distribution and enabling perfect de novo peptide sequencing.

In tandem mass spectrometry of a monovalent (positively charged) tryptic peptide, cleavage mainly occurs at the glutamic acid and the aspartic acid C-termini and the proline N-terminus. Cleavage occurs readily at carboxy-termini of the glutamic acid and the aspartic acid, because the carboxylic acid group provides protons during the cleavage of the neighboring peptide bond. Also, because the nitrogen of the proline acts as a proton receptor, cleavage easily occurs there. Because of the difficulty in moridification of proline, the present invention focuses on chemical modification of the carboxylic group. Additional problems of monovalent tryptic peptide in tandem mass spectrometry are that a peptide containing lysine only has lower mass peaks when compared with a peptide containing arginine, which makes tandem mass spectrometry difficult, and that mistakes may occur during sequencing because the mass of lysine (128.0950 u) is similar to that of glutamine (128.0586 u). To solve these problems, the present invention introduces a two-step chemical modification including guanidination and esterification.

Guanidination turns lysine into homoarginine, thereby improving ionization efficiency of tryptic peptides containing lysine, and increases mass by about 42 Da, thereby preventing confusion with glutamine during peptide sequencing.

Guanidination is effective not only for the tryptic peptides enzymatic cleavaged by trypsin but also for peptides enzymatic cleavaged by a lysine C breakdown enzyme, which generates peptides containing lysine at the carboxy-termini. For example, guanidination may be performed by adding aqueous ammonia and an aqueous guanidination solution to an aqueous solution of protein cleavaged by trypsin (tryptic peptides). The guanidination may be performed using O-methylisourea or S-methylisourea.

Esterification changes carboxylic acid into ester, thereby removing protons to be provided to the neighboring peptide bond and preventing easy breakdown at the carboxy-terminus of the glutamic acid and aspartic acid. However, in the case of methyl-$d_0$ esterification, the mass of the guanidinated lysine becomes equal to that of the methyl-$d_0$ esterified arginine at the carboxy-terminus and the mass of the glutamic acid that has not been chemically modified becomes equal to that of the methyl-$d_0$ esterified aspartic acid. This problem has been solved by using deuterium-substituted methanol-$d_3$ ($CD_3OH$).

Accordingly, the esterification can be performed on at least one selected from the group consisting of carboxyl group of glutamic acid, carboxyl group of aspartic acid, and C-terminus carboxyl group of a peptide.

For the esterification, acetyl chloride or hydrochloric acid catalyst is added to an alcohol having 1 to 5 carbon atoms to prepare a mixture solution. The mixture solution is added to a peptide and esterification is performed at room temperature. Then, the resultant solution is lyophilized.

Preferably, said alcohol is labeled with at least one radioactive isotope selected from the group consisting of carbon and oxygen.

By the chemical modification, lysine is turned to homoarginine and the carboxylic acid of the amino acid is turned to an alkyl ester. In the case that esterification is followed by guanidination, reverse reaction of esterified peptides may occur during the guanidination. Thus, it is more preferable to perform esterification after guanidination.

Guanidination of lysine is carried out with an average yield of at least about 98% and esterification of carboxylic acid is carried out with an average yield of at least about 95%. Under the above-mentioned reaction conditions, said guanidination proceeds without side reactions and said esterification is accompanied by esterification of aspartic acid, a side reaction, of about 15%. However, the resulting side reaction product does not affect the tandem mass spectrometry result because it has a low mass peak.

(c) Maldi Mass Spectrometry and Peptide Sequencing

Following the steps (a) and (b), MALDI mass spectrometry and peptide sequencing may be performed by the conventional method without any specific restrictions.

For example, mass spectrometry of a prepared sample may be performed using a 4700 Proteomics Analyzer, a MALDI tandem mass spectrometer manufactured by Applied Biosystems. Samples ionized by the MALDI process have a monovalent positive charge. The mass spectrometry result may be analyzed with the program developed by Bioinfomatics Solutions Inc. (PEAK 3.0), which is a non-limiting example. During the de novo sequencing, selective modification of each chemical modification site has to be considered. The following modifications occur selectively: esterification at glutamic acid and aspartic acid; guanidination at lysine; esterification at lysine of carboxy-terminus; and esterification at arginine of carboxy-terminus. Since leucine and isoleucine are chemically identical and have the same mass, the de novo sequencing result may be adjusted to express both as leucine (L).

The present invention also provides a method for preparing a sample for MALDI mass spectrometry using electrospraying of a liquid sample and focusing ion optics and an apparatus for the same.

The present invention provides, as an embodiment, a method for preparing a sample for MALDI mass spectrometry that includes the steps of:

(a) mixing a liquid sample with a matrix and electrospraying the mixture to form charged sample particles;

(b) focusing the charged particles with an electromagnetic field using an ion-optical instrument; and (c) collecting the focused charged particles on a solid surface under atmospheric pressure.

In the step (a) of forming charged particles, the liquid sample is an effluent from liquid chromatography or capillary liquid chromatography. In the step (a), the sample particles may be ionized by electrospraying, cold electrospraying, supercooled fluid cluster ionization, electron impact, laser ionization, ICP ionization, etc., but is not limited to these.

The steps (a) and (b) may be performed under atmospheric pressure or in a vacuum.

The sample may be selected from the group consisting of protein, peptide, amino acid, DNA, oligonucleotide, lipid, saccharide, oligosaccharide, glycan, carbohydrate, and polymer.

The matrix used in the step (a) may be dihyroxybenzoic acid (DHB) or α-cyano-4-hydroxycinnamic acid (HCCA).

The present invention further provides an apparatus for preparing a sample for MALDI mass spectrometry that includes:

an electrospraying part that electrosprays a mixture of a liquid sample and a matrix to prepare charged sample particles;

an ion-optics focusing part that focuses the charged particles locally using an electromagnetic field; and a driving part that moves a MALDI sample plate, so that the focused charged particles can be collected on the MALDI sample plate.

The liquid sample is an effluent from liquid chromatography or capillary liquid chromatography and a means for controlling the movement of the MALDI plate may be further included in order to tune with the separation timing of the chromatography.

Figure 10:
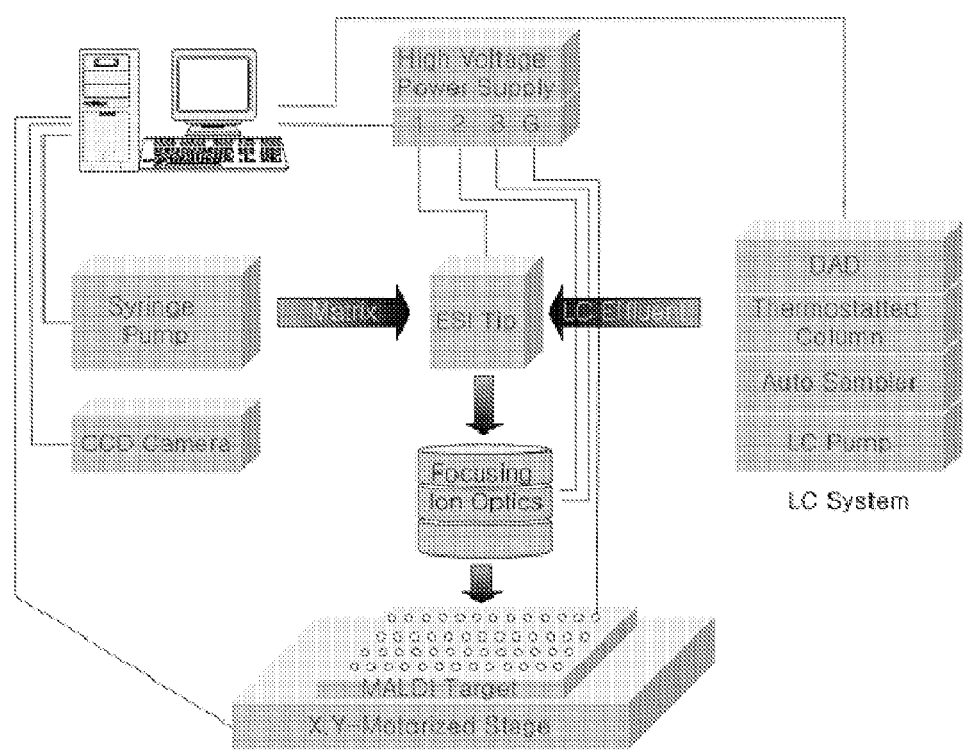
FIG. 10 schematically illustrates the apparatus for mixing an LC effluent and a matrix solution provided from a syringe pump, electrospraying the mixture using an ESI (electrospray ionization) tip, and focusing the resultant charged liquid particles using an ion-optical instrument (focusing ion optics) to coat them on a MALDI target plate. The XY motorized stage moves the multiwell MALDI plate for a given period of time to collect the samples. The CCD camera enables real-time observation of the electrospray at the ESI tip.

The apparatus for focusing the charged liquid particles is illustrated in FIG. 10. The protein or peptide mixture to be sequenced is separated by capillary LC and is electrosprayed as mixed with an acid matrix before the ESI tip. In this process, the solvent is removed and the samples are charged. The charged samples are passed through an electric field generated by the ion-optical instrument under atmospheric pressure and are focused at a single point on the MALDI plate. The MALDI plate, which is placed on the motorized X,Y-stage tuned with the separation timing of the LC, moves gradually to collect the samples at different positions. The samples collected on the MALDI plate are analyzed by a mass spectrometer, such as MALDI-TOF, MALDI-ion trap, and MALDI-FT-ICR, and the analysis data are compared with those of a protein database or MS-Fit database.

Practical and preferred embodiments of the present invention are illustrated in the following examples. However, it will be appreciated that those skilled in the art, in consideration of this disclosure, may make modifications and improvements within the spirit and scope of the present invention.

EXAMPLE 1

In order to confirm the effect of the two-step chemical modification on de novo sequencing, the two-step chemical modification was applied to the well-established bovine serum albumin (BSA) sequencing.

1-1: Treatment and Analysis of BSA

BSA was cleavaged to peptides by porcine trypsin. Two-step chemical modification of guanidination and methyl-$d_0$ (or methyl-$d_3$) esterification was performed on the resulting tryptic peptides. The modified samples were analyzed using a 4700 Proteomics Analyzer, a MALDI tandem mass spectrometer, and then de novo sequenced using PEAKS Studio.

The guanidination was carried out by adding 5.5 µL of aqueous ammonia (7N) and 1.5 µL of an aqueous guanidination solution (O-methylisourea, 10 mg/10 µL) to 5 µL of the tryptic peptide solution and performing the reaction for 10 minutes in an oven at 65° C. 10% (v/v) trifluoroacetic acid was added to terminate the reaction and the solvent was removed by lyophilization. 8 µL of distilled water was added to the dried product and the peptide was purified using PerfectPure C-18 Tip (Eppendorf) and then lyophilized.

For the esterification, a mixture solution was prepared by adding 75 µL of acetyl chloride to 500 µL of methanol that had been cooled to −25° C. 40 µL of the mixture solution was added to the purified and dried peptide. After esterification at room temperature for 1 hour, the reaction was terminated by lyophilization.

The resulting samples were analyzed with a 4700 Proteomics Analyzer, a MALDI tandem mass spectrometer manufactured by Applied Biosystems. By the MALDI process, the samples are ionized and have a positive monovalent charge. The mass spectrometry result was analyzed using the program of Bioinfomatics Solutions Inc. (PEAK 3.0).

1-2: Observation of Peptides after Chemical Modification

BSA was treated with trypsin in the same manner as in EXAMPLE 1-1 and analyzed with a 4700 Proteomics Analyzer, without chemical modification. The result is shown in (a) of FIG. 2.

A BSA fragment cleavaged by trypsin was guanidinated in the same manner as in EXAMPLE 1-1 and analyzed with a 4700 Proteomics Analyzer. The result is shown in (b) of FIG. 2.

A BSA fragment cleavaged by trypsin was guanidinated and then esterified in the same manner as in EXAMPLE 1-1 and analyzed with a 4700 Proteomics Analyzer. The result is shown in (c) of FIG. 2.

Figure 2:
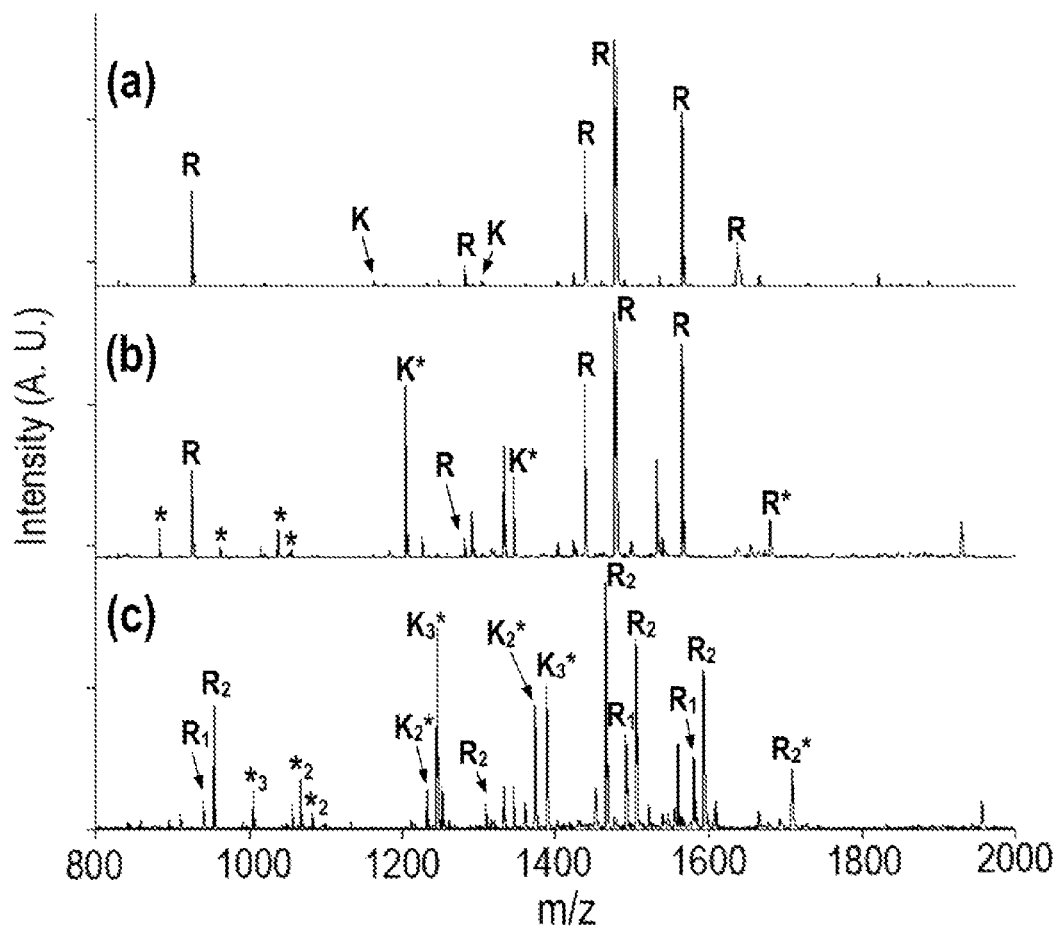
FIG. 2 shows the mass spectra of tryptic peptides of bovine serum albumin (BSA), which have been chemically modified in two steps: (a) before chemical modification, (b) after guanidination only, and (c) after guanidination and methyl-$d_0$ esterification.

FIG. 2 shows the mass spectra of tryptic peptides of bovine serum albumin (BSA) that have been chemically modified in two steps: (a) before chemical modification, (b) after guanidination only, and (c) after guanidination and methyl-$d_0$ esterification. R is for the case where the carboxy-terminus of the tryptic peptide is arginine and K is for the case where the carboxy-terminus of the tryptic peptide is lysine. "*" represents peptides showing increase in peak size after guanidination. The subscript figures stand for the number of esterification.

Comparing (a) with (b), it is confirmed that mass peaks of peptides having lysine increased after guanidination. From (c), it is can be seen how many acidic residues were included into each peptide by esterification.

1-3: HLVDEPQNLIK(SEQ ID NO: 1) Sequencing

Figure 3:
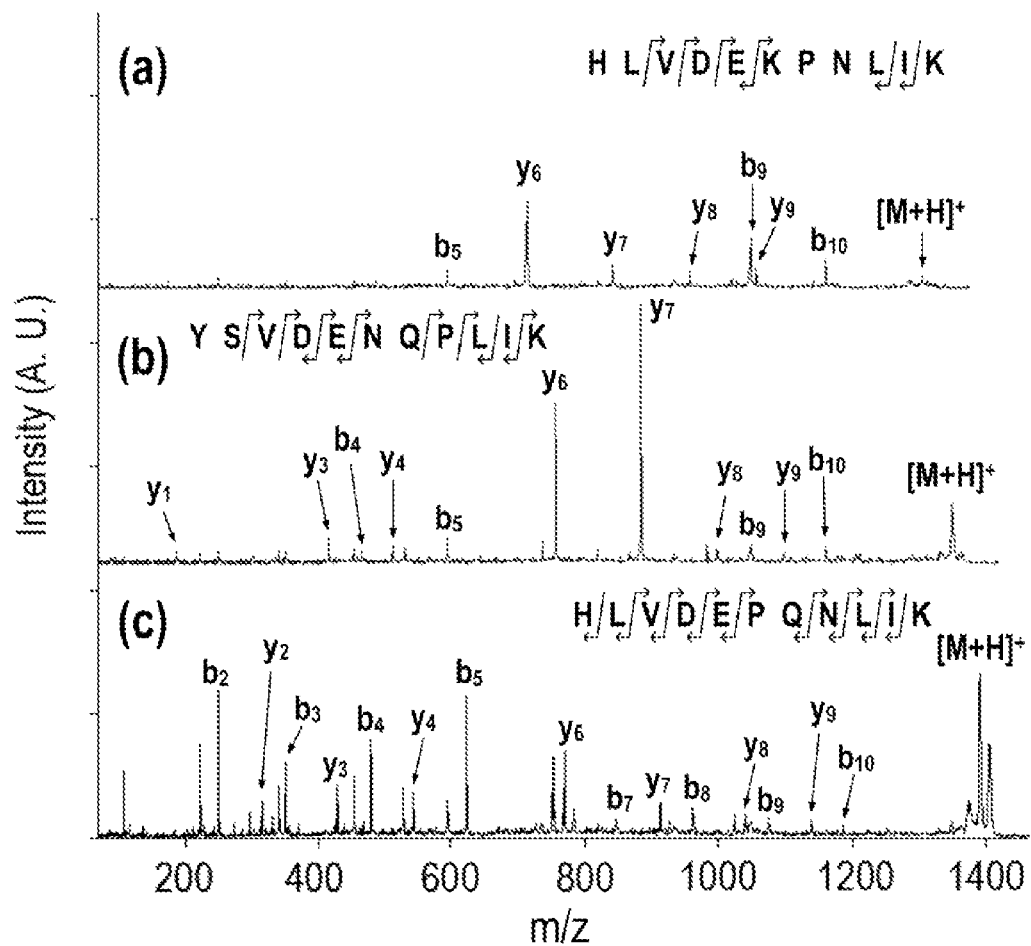
FIG. 3 shows the tandem mass spectra of tryptic peptides of BSA having HLVDEPQNLIK(SEQ ID NO: 1) sequence, which have been chemically modified in two steps: (a) before chemical modification, (b) after guanidination, and (c) after guanidination and methyl-$d_0$ esterification.

BSA was treated with trypsin, guanidinated, and esterificated in a similar method as in EXAMPLE 1-2. Ions to be analyzed were selected from the resulting samples and tandem mass spectrometry was performed. The result is shown in FIG. 3. If the mass of the particular ion to be analyzed is input, other ions are removed from the analysis instrument (in a gas phase) and only the wanted ion is cleavaged and analyzed in a gas phase.

FIG. 3 shows the tandem mass spectra of tryptic peptides of BSA having HLVDEPQNLIK(SEQ ID NO: 1) sequence that have been chemically modified in two steps: (a) before chemical modification, (b) after guanidination, and (c) after guanidination and methyl-$d_0$ esterification.

When chemical modification was not performed, as in (a), the number of daughter ions was smaller because cleavage occurs selectively at around the carboxyl groups of glutamic acid and aspartic acid of the carboxy-terminus. As a result, the peptide was mis-sequenced as HLVDEKPNLIK. When guanidination was performed, as in (b), lysine of the carboxy-terminus was turned to homoarginine, thereby improving ionization efficiency and detection sensitivity during the tandem mass spectrometry. However, only two more daughter ions were produced and cleavage still occurred selectively at the carboxyl-terminus. As a result, the peptide was mis-sequenced as YSVDENQPLIK(SEQ ID NO: 5). That is, although guanidination improves detection sensitivity of peptides, it is limited in enabling perfect peptide sequencing. When esterification followed the guanidination, as in (c), detection sensitivity of parent ions was improved by the guanidination and the problem of selective cleavage around the carboxylic acid was solved by the esterification since the carboxylic acid was turned to methyl ester. As a result, a variety of daughter ions were observed and exact sequencing (HLVDEPQNLIK; SEQ ID NO: 1) was obtained.

1-4: AEFVEVTK(SEQ ID NO: 2) Sequencing

Figure 4:
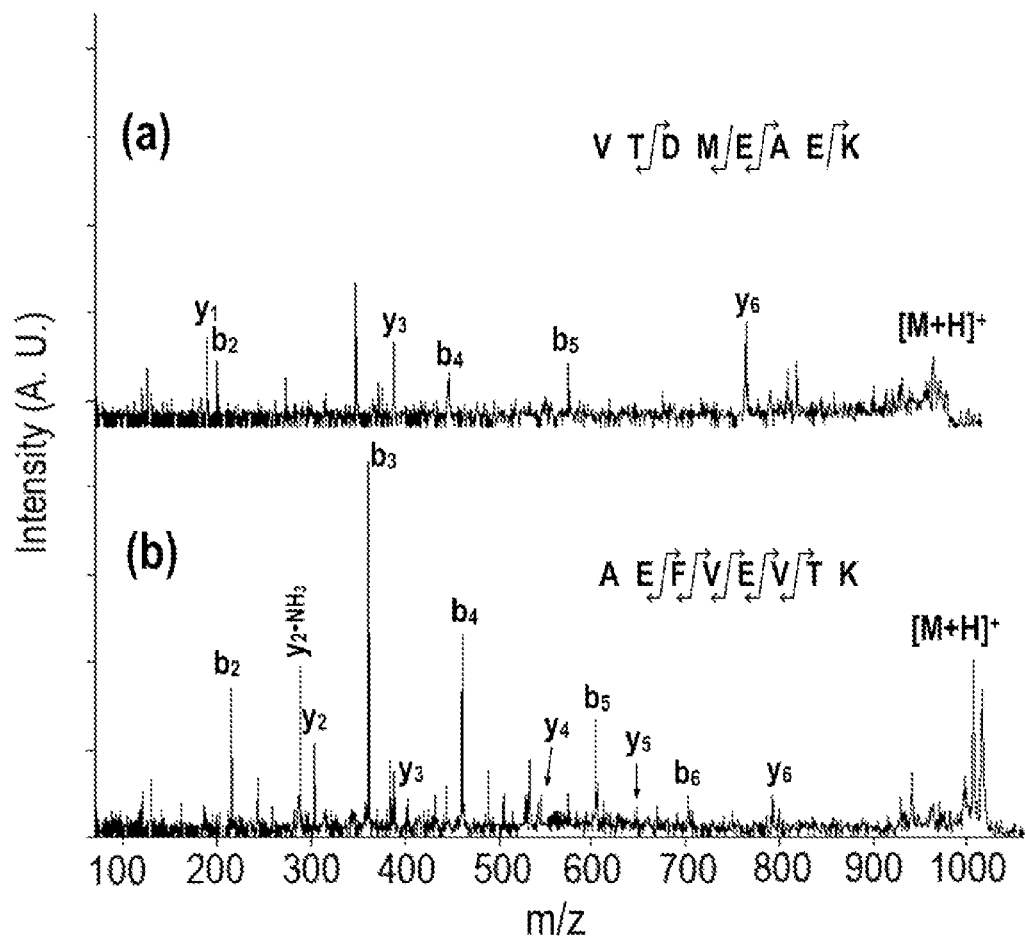
FIG. 4 shows the tandem mass spectra of tryptic peptides of BSA having AEFVEVTK(SEQ ID NO: 2) sequence, which have been chemically modified in two steps: (a) after guanidination only and (b) after guanidination and methyl-$d_0$ esterification.

Sample preparation was performed in the same manner as in EXAMPLE 1-3, with a different peptide fragment. FIG. 4 shows the tandem mass spectra of tryptic peptides of BSA having AEFVEVTK(SEQ ID NO: 2) sequence that have been chemically modified in two steps: (a) after guanidination only and (b) after guanidination and methyl-$d_0$ esterification. When chemical modification was not performed, tandem mass spectrometry was impossible because the parent ion itself was not observed, which was caused by poor ionization efficiency due to the lysine contained in the carboxy-terminus. After guanidination, tandem mass spectrometry was possible as detection sensitivity of the parent ion improved. However, as seen in FIG. 4(a), cleavage occurred selectively, giving specific daughter ions. As a result, the peptide was mis-sequenced as VTDMEAEK(SEQ ID NO: 6). When the carboxylic acid was turned to methyl ester by esterification, FIG. 4(b), a variety of daughter ions were observed and exact de novo sequencing (AEFVEVTK; SEQ ID NO: 2) was obtained.

1-5: YLYEIAR(SEQ ID NO: 3) Sequencing

Figure 5:
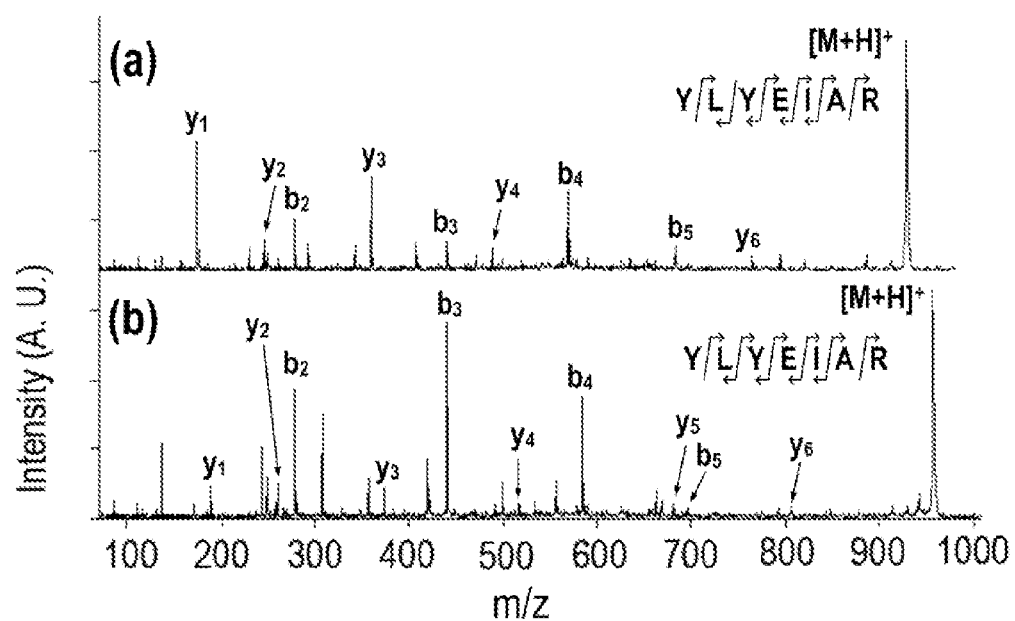
FIG. 5 shows the tandem mass spectra of tryptic peptides of BSA having YLYEIAR(SEQ ID NO: 3) sequence, which have been chemically modified in two steps: (a) before chemical modification and (b) after methyl-$d_0$ esterification.

Sample preparation was performed in the same manner as in EXAMPLE 1-3, however with different peptide fragment. FIG. 5 shows the tandem mass spectra of tryptic peptides of BSA having YLYEIAR(SEQ ID NO: 3) sequence, which have been chemically modified in two steps: (a) before chemical modification, (b) after methyl-$d_0$ esterification. From FIG. 5, the effect of chemical modification of the peptide containing arginine at the carboxy-terminus can be confirmed. Guanidination is of no effect, because there is no lysine. Because arginine and homoarginine has the same functional groups and are different only in residue length, the spectra are similar to those of the peptide having guanidinated lysine. Before esterification (a), y-type daughter ions ($y_1$, $y_3$) cleaved by the carboxylic acid group of carboxylic acid and glutamic acid at the carboxy-terminus were dominant, thereby making de novo sequencing difficult. However, after esterification (b), the y-type daughter ions showed uniform size and distribution and b-type ions were detected well, too, thereby making de novo sequencing easier.

De novo sequencing result of the tandem mass spectrometry on the tryptic peptides of BSA before and after chemical modification analyzed with PEAKS Studio is given in Table 1. Before chemical modification, the peptide containing lysine only at the carboxy-terminus was not analyzed or analyzed with poor reliability, because of lack of parent ions. The peptide having the LVNELTEFAK(SEQ ID NO: 7) sequence and the peptide having the HLVDEPQNLIK(SEQ ID NO: 1) sequence were analyzed correctly on the whole, but there were some errors because of insufficient daughter ion strength. As for AEFVEVTK(SEQ ID NO: 2), sequencing itself was impossible because even the parent ion was not detected. The YLYEIAR(SEQ ID NO: 3) peptide containing arginine at the carboxy-terminus showed superior signal strength, although distribution of the daughter ion strength was not uniform, and a high sequencing reliability of 97.7% was obtained.

When guanidination was performed only, sequencing of AEFVEVTK(SEQ ID NO: 2) became possible, but the sequencing reliability was only 15.5%. Other peptides containing lysine showed stronger parent ion strength but sequencing reliability was still low because of selective cleavage at specific sites. In particular, the guanidinated HLVDEPQNLIK(SEQ ID NO: 1) peptide showed poorer de novo sequencing result than before guanidination. From this, it is understood that a satisfactory peptide sequencing cannot be obtained with guanidination only.

When guanidination was followed by esterification using methanol-$d_0$ ($CH_3OH$), the peptides having LVNELTEFAK (SEQ ID NO: 7), YLYEIAR(SEQ ID NO: 3) and HLVDEPQNLIK(SEQ ID NO: 1) sequences were analyzed correctly. For AEFVEVTK(SEQ ID NO: 2), the FVEVTK (SEQ ID NO: 8) sequence was analyzed correctly, except that the first two amino acids were analyzed in reverse order. This is an outstanding result considering that the AEFVEVTK (SEQ ID NO: 2) sequence was not analyzed at all before the two-step chemical modification.

The low reliability of about 46% for YLYEIAR(SEQ ID NO: 3) and HLVDEPQNLIK(SEQ ID NO: 1) is due to the fact that the mass of esterified aspartic acid happens to be identical to that of unmodified glutamic acid and the mass of guanidinated lysine happens to be identical to that of esterified arginine, lowering the reliability to half. It is expected that accurate peptide sequencing will be possible with the two-step chemical modification if this problem is solved.

The problem of mass coincidence can be solved by using deuterium-substituted methanol-$d_3$ ($CD_3OH$) in the esterification. The result is also given in Table 1. When methanol-$d_3$ ($CD_3OH$) was used, the sequencing reliability was improved to 99% and 92% for YLYEIAR(SEQ ID NO: 3) and HLVDEPQNLIK(SEQ ID NO: 1), respectively. Comparing this result to that prior to the chemical modification, it is confirmed that the two-step chemical modification of guanidination and methyl-$d_3$ esterification significantly improves the reliability of de novo sequencing. In Table 1, the superscript g stands for guanidinated amino acid and the superscript m stands for methyl-$d_0$ or methyl-$d_3$ esterified amino acid. The percentages stand for reliability. In the de novo sequencing result, both leucine and isoleucine were expressed as leucine (L).

TABLE 1

| | De novo sequencing result | | | |
|---|---|---|---|---|
| Amino acid sequence | Before chemical modification | After guanidination | After guanidination and methyl-$d_0$ esterification | After guanidination and methyl-$d_3$ esterification |
| YLYEIAR (SEQ ID NO: 3) | YLYELAR (SEQ ID NO: 3) 97.7% LY<u>YE</u>LAR 2.3% (SEQ ID NO: 73) | | YLY$E^m$LA$R^m$ 49.3% (SEQ ID NO: 9) YL<u>Y$E^m$</u>LA$K^g$ 49.3% (SEQ ID NO: 11) LY<u>Y$E^m$</u>LA$K^g$ 1% | YLY$E^m$LA$R^m$ 99% (SEQ ID NO: 10) LY<u>Y$E^m$</u>LA$R^m$ 1% (SEQ ID NO: 13) |

TABLE 1-continued

|  | De novo sequencing result | | | |
|---|---|---|---|---|
| Amino acid sequence | Before chemical modification | After guanidination | After guanidination and methyl-$d_0$ esterification | After guanidination and methyl-$d_3$ esterification |
| AEFVEVTK (SEQ ID NO: 2) | N/A | VTDMEAE$K^g$ 27.2% (SEQ ID NO: 15) AEFVEVT$K^g$ 15.5% (SEQ ID NO: 16) | (SEQ ID NO: 14) LYY$E^m$LA$R^m$ 1% (SEQ ID NO: 12) $E^m$AFV$E^m$VT$K^{gm}$ 59.9% (SEQ ID NO: 17) A$E^m$FV$E^m$VT$K^{gm}$ 28.6% (SEQ ID NO: 18) VDFV$E^m$VT$K^{gm}$ 7.7% (SEQ ID NO: 19) | A$E^m$FV$E^m$VT$K^{gm}$ 92.5% (SEQ ID NO: 20) $E^m$AFV$E^m$VT$K^{gm}$ 7.5% (SEQ ID NO: 21) |
| LVNELTEFAK (SEQ ID NO: 7) | VLNELTEFAK 99% (SEQ ID NO: 22) LVNELTEFAK 1% (SEQ ID NO: 7) | VLNELVMFA$K^g$ 40.9% (SEQ ID NO: 23) VLNELTEFA$K^g$ 37.6% (SEQ ID NO: 24) LVNELTEFA$K^g$ 10.3% (SEQ ID NO: 25) | LVN$E^m$LT$E^m$FA$K^{gm}$ 86.7% (SEQ ID NO: 26) VLN$E^m$LT$E^m$FA$K^{gm}$ 13.3% (SEQ ID NO: 27) | LVN$E^m$LT$E^m$FA$K^{gm}$ 82.6% (SEQ ID NO: 28) VLN$E^m$LT$E^m$FA$K^{gm}$ 17.2% (SEQ ID NO: 29) |
| HLVDEPQNLIK (SEQ ID NO: 1) | HLVDEKPNLLK 36.4% (SEQ ID NO: 30) HLVDEPKNLLK 29.3% (SEQ ID NO: 31) HLVDEPQNLLK 14.2% (SEQ ID NO: 32) | YSVDENQPLL$K^g$ 44.4% (SEQ ID NO: 33) YSVDEELPLL$K^g$ 41.8% (SEQ ID NO: 34) YSVDELEPLL$K^g$ 4.1% (SEQ ID NO: 35) | HLV$D^m E^m$PQNLL$K^{gm}$ 48.3% (SEQ ID NO: 36) HLV$EE^m$PQNLL$K^{gm}$ 48.3% (SEQ ID NO: 37) LHV$D^m E^m$PQNLL$K^{gm}$ 1.2% (SEQ ID NO: 38) LHV$EE^m$PQNLL$K^{gm}$ 1.2% (SEQ ID NO: 39) | HLV$D^m E^m$PQNLL$K^{gm}$ 91.9% (SEQ ID NO: 40) HLV$D^m E^m$PKNLL$K^{gm}$ 4.5% (SEQ ID NO: 41) |

EXAMPLE 2

Two-step chemical modification of guanidination and methyl-$d_3$ esterification was applied to sequencing of the proteins extracted from yeast in order to confirm the applicability of the two-step chemical modification in actual de novo sequencing.

2-1: Extraction of Proteins from Yeast

Proteins were extracted from yeast whole cell extract-prt part by chromatin immunoprecipitation as follows.

1) Prepare 100 mL of cultures ($OD_{600} \approx 1.2$-1.5)
2) Crosslink
Add 2.7 mL of 37% HCHO (final conc.: ~1%)
Shake gently for 2 hrs at R.T.
3) Harvest and resuspend cells with 800 ul of lysis buffer.
4) Freeze with liquid nitrogen and thaw at R.T. (×4)
5) Shear chromatin
Sonicate extracts for 10× 10 sec pulses.
In between 10 sec pulses, let samples sit on ice for 1-2 min.
6) Clarify samples
Centrifuge at max speed for 10 min and 15 min at 4° C.
7) Measure the volume
8) Immunoprecipitae (IP) rest of lysate and 50 ul of Anti-HA affinity matrix (3 hrs~)
Spin beads down gently at 3-7.5 K for 1-2 min.
9) Wash immunoprecipitates
1× with 1 mL of IP2, IP3, IP4.5 for 5 min each.
2× with 1 mL of TE
10) Elute Immunoprecipitates
Add 100 ul of 1% SDS+TE, incubate at 65° C., 15 min
Centrifuge briefly (max speed) and transfer sup.
Wash beads with 50 ul of 1% SDS+TE, cfg and add.
11) Reverse cross-link; Incubate IPs and SM for $\geq$6 hrs at 65° C.

TABLE 2

| IP3 Buffer | 0.1% | SDS | 0.1 mL of 10% |
|---|---|---|---|
|  | 1% | Triton | 1 mL of 10% |
|  | 2 mM | EDTA | 40 ul of 0.5 M |
|  | 20 mM | Tris 8.0 | 0.2 mL of 1 M |
|  | 500 mM | NaCl | 5 mL of 1 M |
|  |  | $dH_2O$ | 3.66 mL |
|  |  | Total | 10 mL |
| IP4.5 Buffer | 0.5% | DOC | 0.5 mL of 10% |
|  | 0.5% | NP-40 | 0.5 mL of 10% |
|  | 1 mM | EDTA | 20 ul of 0.5 M |
|  | 10 mM | Tris 8.0 | 0.1 mL of 1 M |
|  | 250 mM | LiCl | 1.25 mL of 2 M |
|  |  | $dH_2O$ | 7.63 mL |
|  |  | Total | 10 mL |
| TE | 10 mM | Tris 8.0 | 0.1 mL of 1 M |
|  | 1 ml | EDTA | 20 ul of 0.5 M |
|  |  | $dH_2O$ | 9.88 mL |
|  |  | Total | 10 mL |
| 1% SDS + TE | 10 mM | Tris 8.0 | 0.1 mL of 1 M |
|  | 1 mM | EDTA | 20 ul of 0.5 M |
|  | 1% | SDS | 1 mL of 10% |
|  |  | $dH_2O$ | 8.88 mL |
|  |  | Total | 10 mL |

2-2: Separation of Sample Proteins

Of the proteins extracted from yeast, the proteins labeled with human influenza hemagglutinin (HA) or the proteins that bind with them were separated by immunoprecipitation using an anti-HA affinity matrix. Subsequently, 1-D gel electrophoresis (1-D SDS PAGE) was carried out. Silver staining was carried out (Silver Stain Plus Kit, Bio-Rad). When protein spots appeared, the silver staining was stopped using 5% acetic acid. The gel band of the sample protein was excised and destained, cleavaged by in-gel digestion using trypsin and extracted from the gel in the form of peptide. The in gel digestion was carried out as follows.

1. Excise the band of interest with clean scalpel and transfer the gel slice into e-tube.
2. Destain
   1) Prepare two stock solutions of 30 mM $K_3Fe(CN)_6$ (potassium ferricyanide) and 100 mM $Na_2S_2O_3$ (sodiumthiosulfate), both dissolved in water.
   2) Prepare a working solution by mixing a 1:1 ratio of the above stock solutions.
   3) Add 50 ul of the working solution to cover the gel bands.
   (The stain intensity was monitored until the brownish color disappeared and changed to yellow.)
   4) Rinse the gel band a few times with $dH_2O$ to stop the reaction.
   5) Add 100 ul of 200 mM $NH_4HCO_3$ to cover the gel for 20 min and discard this solution.
   6) Cut and smash the gel into small pieces and wash them with water.
3. Add 50 ul of 100 mM $NH_4HCO_3$ to wash the gel pieces for 10 min, and then add 50 ul of ACN for 10 min to dehydrate the gel pieces. (×2)
4. Dry the squeezed gel particle by speed vacuum for 30 min to remove remaining solvent.
5. Treat with trypsin
   1) Add the digestion buffer (44 ul of 50 mM $NH_4HCO_3$ and 6 ul of 0.1 ug/ul trypsin) in an ice-cold bath for 50 min.
   2) Remove supernatant and add 10 ul of 50 mM $NH_4HCO_3$ (37° C., overnight; 12-16 hrs).
6. Extract
   1) Add 30 ul of 20 mM $NH_4HCO_3$ for 5 min (×1) and then add 30 ul of 5% formic acid in 50% ACN for 20 min (×3).
   2) Freeze with liquid $N_2$ and dry down by mechanical pump. (Roll up the tube with parafilm and make a hole.)

2-3: Peptide Sequencing

Two-step chemical modification of guanidination and methyl-$d_3$ esterification was performed on the resulting peptides. The chemically modified samples were analyzed with 4700 Proteomics Analyzer, a MALDI tandem mass spectrometer, and de novo sequenced using PEAKS Studio.

Figure 6:
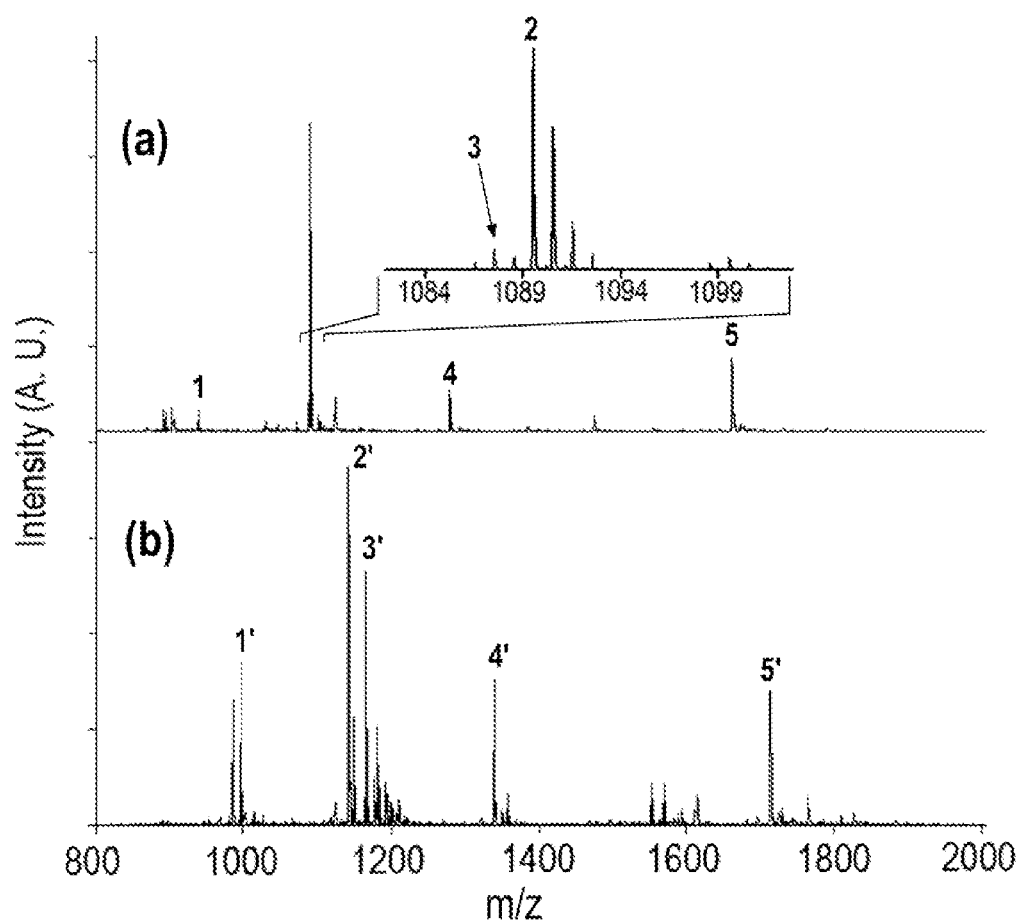
FIG. 6 shows the tandem mass spectra of tryptic peptides of Tgl2 protein of yeast to which HA tags separated by human influenza hemagglutinin (HA) immunoprecipitation are attached, which has been chemically modified in two steps: (a) before chemical modification and (b) after guanidination and methyl-$d_3$ esterification. The numbers 1, 2, 3, 4, and 5 represent the peptides that have not been chemically modified, while the numbers 1', 2', 3', 4', and 5' represent the peptides that have been chemically modified in two steps.

FIG. 6 shows the tandem mass spectra of the tryptic peptides of yeast separated by human influenza hemagglutinin (HA) immunoprecipitation, which was chemically modified in two steps: (a) before chemical modification, (b) after guanidination and methyl-$d_3$ esterification. Peptides No. 1, 2, 3, 4 and 5 were identifies as follows: No. 1=LQDDWSK(SEQ ID NO: 42); No. 2=VPGFGSLEER(SEQ ID NO: 43); No. 3=AMALDAQLQK(SEQ ID NO: 44); No. 4=YFNLVTPNSPK(SEQ ID NO: 45); No. 5=TSGSPGLQEFPEAWR (SEQ ID NO: 46). As in FIG. 2, the tryptic peptides containing lysine at the carboxy-terminus had low mass peaks before the two-step chemical modification but the peak size increased after the two-step chemical modification. In particular, the peptide No. 3, which had low mass peak because of lysine and could not be detected easily because it was neighboring the high mass peak of the peptide No. 2, showed significant increase in peak size after the two-step chemical modification and could be discerned from the peptide No. 2.

Figure 7:
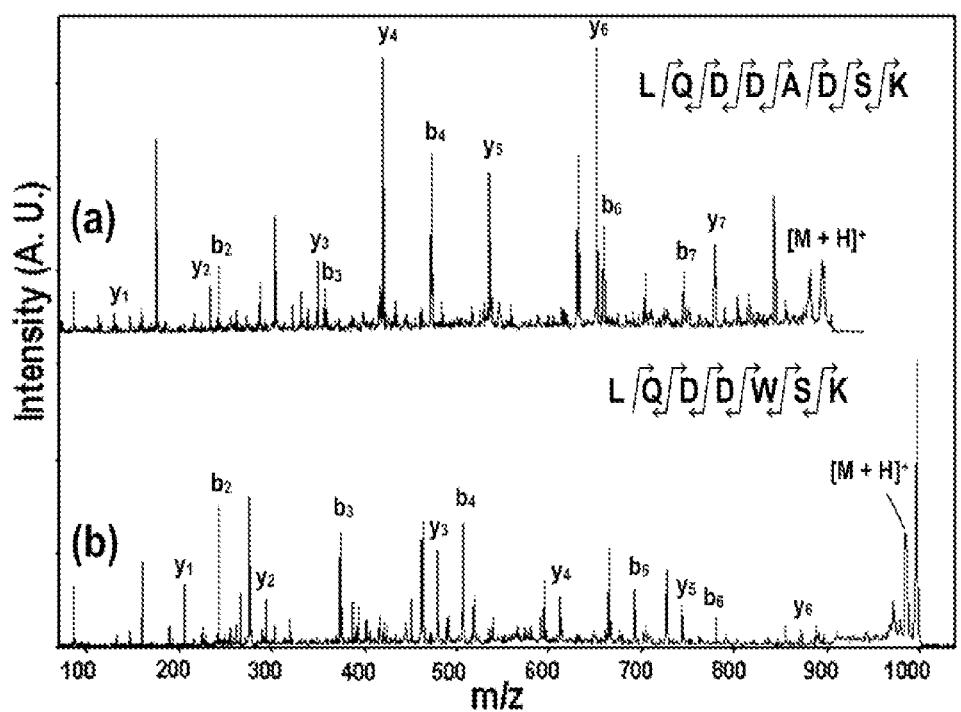
FIG. 7 shows the tandem mass spectra of No. 1 peptide of FIG. 6, which have been chemically modified in two steps: (a) before chemical modification and (b) after chemical modification.

FIG. 7 shows the tandem mass spectra of the peptide No. 1 of FIG. 6, which have been chemically modified in two steps: (a) before chemical modification, (b) after chemical modification. Before the two-step chemical modification (a), the daughter ions formed by cleavage near the carboxylic acid of aspartic acid were dominant, thereby resulting in mis-sequencing as LQDDADSK(SEQ ID NO: 47). However, after the two-step chemical modification (b), all the daughter ions were observed uniformly because the carboxylic acid was turned to methyl ester by esterification. As a result, an accurate de novo sequencing of LQDDWSK(SEQ ID NO: 42) could be obtained.

Figure 8:
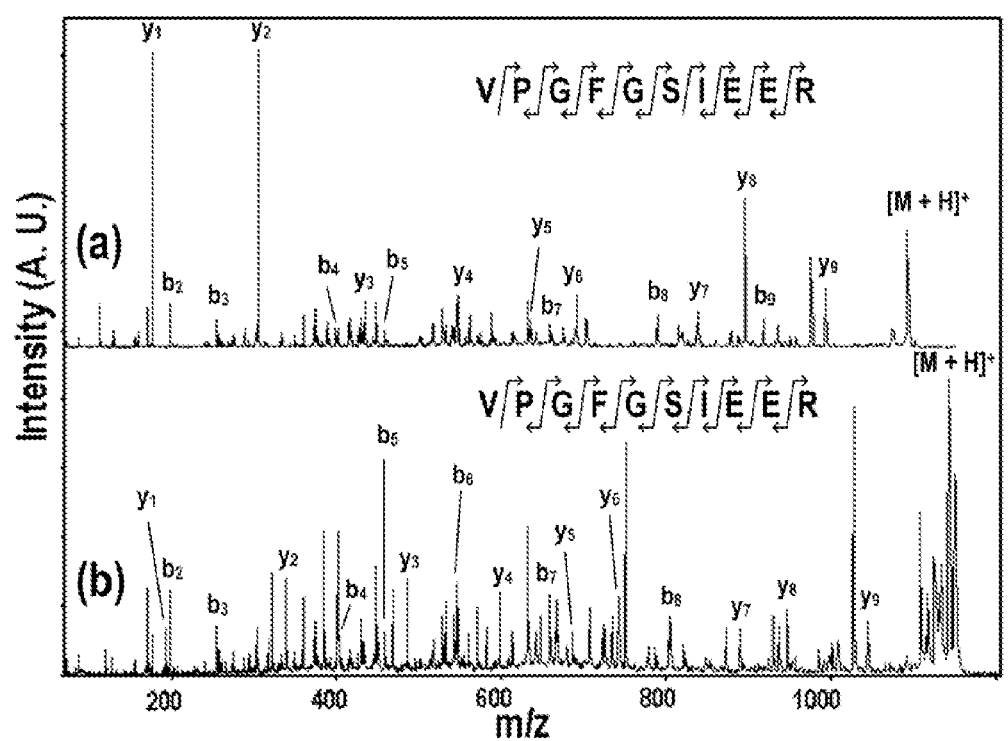
FIG. 8 shows the tandem mass spectra of No. 2 peptide of FIG. 6, which have been chemically modified in two steps: (a) before chemical modification and (b) after chemical modification.

FIG. 8 shows the tandem mass spectra of the peptide No. 2 of FIG. 6, which was chemically modified in two steps: (a) before chemical modification, (b) after chemical modification. Before the two-step chemical modification (a), the daughter ions formed by cleavage near the carboxylic acid of glutamic acid were dominant. Although specific daughter ions were dominant, an accurate sequencing of VPGFGSLEER(SEQ ID NO: 43) was possible because there were a lot of parent ions. After the two-step chemical modification (b), all the daughter ions were observed uniformly because the carboxylic acid was turned to methyl ester by esterification. As a result, an accurate de novo sequencing of LQDDWSK(SEQ ID NO: 42) could be obtained.

Figure 9:
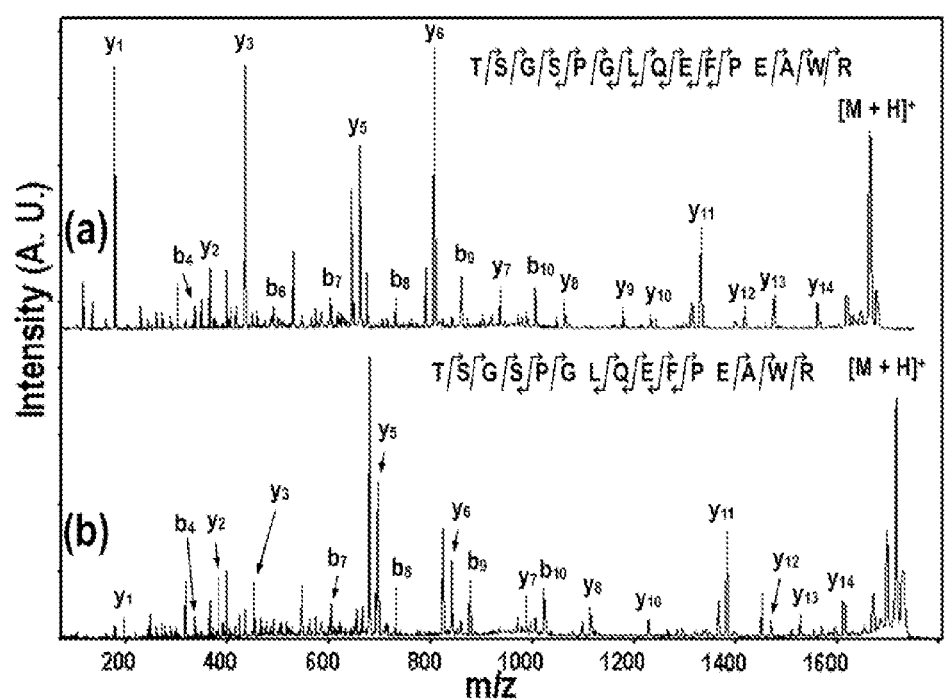
FIG. 9 shows the tandem mass spectra of No. 5 peptide of FIG. 6, which have been chemically modified in two steps: (a) before chemical modification and (b) after chemical modification.

FIG. 9 shows the tandem mass spectra of the peptide No. 5 of FIG. 6, which was chemically modified in two steps: (a) before chemical modification, (b) after chemical modification. Before the two-step chemical modification (a), the daughter ions formed by cleavage near the carboxylic acid of aspartic acid were dominant but accurate sequencing of TSGSPGLQEFPEAWR(SEQ ID NO: 46) was possible. However, after the two-step chemical modification (b), all the daughter ions were observed uniformly, except for $y_5$ formed by proline, because the carboxylic acid was turned to methyl ester by esterification. As a result, an accurate de novo sequencing of TSGSPGLQEFPEAWR(SEQ ID NO: 46) could be obtained as in (a).

The peptides No. 3 and 4 of FIG. 6 were sequenced as AMALDAQLQK(SEQ ID NO: 44) and YFNLVTPNSPK (SEQ ID NO: 45), respectively, by the method proposed in the present invention.

From the de novo sequencing result, it was confirmed that the peptides No. 1, 2, 3 and 4 are from the Tgl2 protein of yeast. However, the peptide No. 5 was irrelevant of yeast. The peptide No. 5 was identified as the fusion peptide, which was used to link the HA-tag to the promoter of Tgl2, but could not be found in the database for HA-tag or yeast genes. This confirms that the present invention enables accurate peptide sequencing without referring to the gene database through de novo sequencing only.

Table 3 shows the de novo sequencing result on the peptides No. 1, 2, 3, 4 and 5 of FIG. 6 using the two-step chemical modification. The superscript g stands for the guanidinated amino acid and the superscript m stands for the methyl-$d_0$ or methyl-$d_3$ esterified amino acid. The percentages stand for reliability. In the de novo sequencing result, both leucine and isoleucine were expressed as leucine (L). Before the chemical modification, the peptide containing lysine only without arginine was not analyzed or analyzed with poor sequencing reliability because of lack of parent ions, as for BSA in EXAMPLE 1. For the peptide having LQDDWSK(SEQ ID NO: 42) sequence and the peptide having YFNLVTPNSPK (SEQ ID NO: 45) sequence, most of the amino acid was analyzed accurately, but there were some errors because of insufficient daughter ion strength. The peptide having AMALDAQLQK(SEQ ID NO: 44) sequence could not be sequenced by tandem mass spectrometry because the mass peak was neighboring the high peak of the peptide having VPGFGSIEER(SEQ ID NO: 48) sequence. The peptide containing arginine and having VPGFGSIEER(SEQ ID NO: 48) sequence and the peptide having TSGSPGLQEFPEAWR (SEQ ID NO: 46) sequence could be sequenced with good reliability of 99% because of superior signal strength, although distribution of the daughter ion strength was not uniform.

After the two-step chemical modification, all the peptides except for the peptide having AMALDAQLQK(SEQ ID NO: 44) sequence showed very high de novo sequencing reliability of 99%. For the peptide having AMALDAQLQK(SEQ ID NO: 44) sequence, perfect sequencing was impossible because the daughter ion formed by cleavage between A and M was not detected. But, except for the first two amino acids, other amino acid sequence was accurately analyzed with a reliability of 99%.

TABLE 3

| Actual amino acid sequence of Tgl2p | De novo sequencing result | | | |
|---|---|---|---|---|
| | Before chemical modification | | After guanidination and methyl-$d_3$ esterification | |
| LQDDWSK (SEQ ID NO: 42) | LQDDADSK (SEQ ID NO: 47) | 71% | LQ$D^mD^m$WS$K^{gm}$ (SEQ ID NO: 55) | 99% |
| | LQDDWSK (SEQ ID NO: 42) | 27.6% | LK$D^mD^m$WS$K^{gm}$ (SEQ ID NO: 56) | 1% |
| | LKDDWSK (SEQ ID NO: 49) | 1% | LQ$D^mD^m$DAS$K^{gm}$ (SEQ ID NO: 57) | 1% |
| VPGFGSIEER (SEQ ID NO: 48) | VPGFGSLEER (SEQ ID NO: 43) | 99% | VPGFGSL$E^mE^mR^m$ (SEQ ID NO: 58) | 99% |
| | VGPFGSLEER (SEQ ID NO: 50) | 1% | VPFGGSL$E^mE^mR^m$ (SEQ ID NO: 59) | 1% |
| | VPGFGSNQER (SEQ ID NO: 51) | 1% | VPGFGSL$E^m$D$K^{gm}$ (SEQ ID NO: 60) | 1% |
| AMALDAQLQK (SEQ ID NO: 44) | | | MA$ALD^m$AQLQ$K^{gm}$ (SEQ ID NO: 61) | 61.9% |
| | | | TT$ALD^m$AQLQ$K^{gm}$ (SEQ ID NO: 62) | 18.5% |
| | | | AMAL$D^m$AQLQ$K^{gm}$ (SEQ ID NO: 63) | 6.2% |
| YFNLVTPNSPK (SEQ ID NO: 45) | YFNLVTNPSPK (SEQ ID NO: 52) | 99% | YFNLVTPNSP$K^{gm}$ (SEQ ID NO: 64) | 99% |
| | YFNLVTPNSPK (SEQ ID NO: 45) | 1% | YFGGVTPNSP$K^{gm}$ (SEQ ID NO: 65) | 1% |
| TSGSPGLQEFPEAWR (SEQ ID NO: 46) | TSGSPGLQEFPEAWR (SEQ ID NO: 46) | 99% | TSGSPGLQ$E^m$FP$E^m$AW$R^m$ (SEQ ID NO: 66) | 99% |
| | TSGSGPLQEFPEAWR (SEQ ID NO: 53) | 1% | TSGSPGLK$E^m$FP$E^m$AW$R^m$ (SEQ ID NO: 67) | 1% |
| | TSGSPGLQEFPEADAR (SEQ ID NO: 54) | 1% | TSGSPGLQ$E^m$FSRAW$R^m$ (SEQ ID NO: 68) | 1% |

As confirmed above, the present invention enables perfect de novo sequencing of tryptic peptide samples taken from lives without depending on the gene database, because detection sensitivity of the peptide increases and the daughter ions can be detected uniformly during tandem mass spectrometry due to the two-step chemical modification. Also, as seen in FIG. 9, even a peptide not listed in the database can be sequenced perfectly and accurately.

EXAMPLE 3

Figure 11:
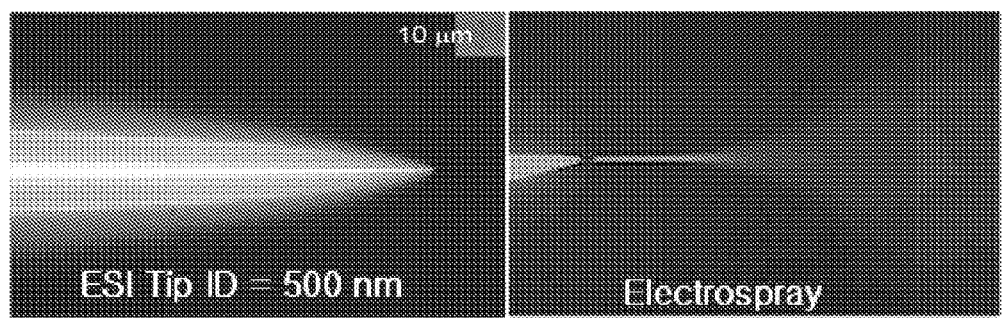
FIG. 11 shows the liquid sample electrosprayed at the ESI tip.

FIG. 11 shows the liquid sample electrosprayed at the ESI tip. Inner diameter of the ESI tip ranged from 500 nm to 30 mm. Flow rate of the liquid sample was controlled within from 200 mL to 2 mL per minute.

EXAMPLE 4

Figure 12:
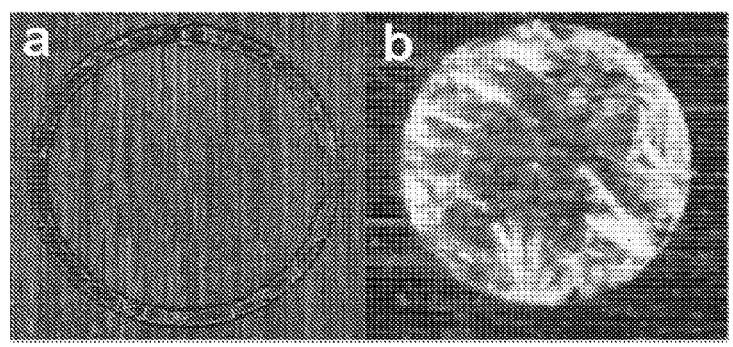
FIG. 12a shows the MALDI sample prepared using DHB (dihydroxybenzoic acid) as a matrix in accordance with the present invention and FIG. 12b shows the MALDI sample prepared by the conventional dried droplet technique.

FIG. 12a shows the MALDI sample prepared using DHB (dihydroxybenzoic acid) as matrix in accordance with the present invention. FIG. 12b shows the MALDI sample prepared by the conventional dried droplet technique. While the sample of FIG. 12b has very rough surface and has large and non-uniform crystal particles, the sample of FIG. 12a has fine and uniform crystal particles.

Figure 13:
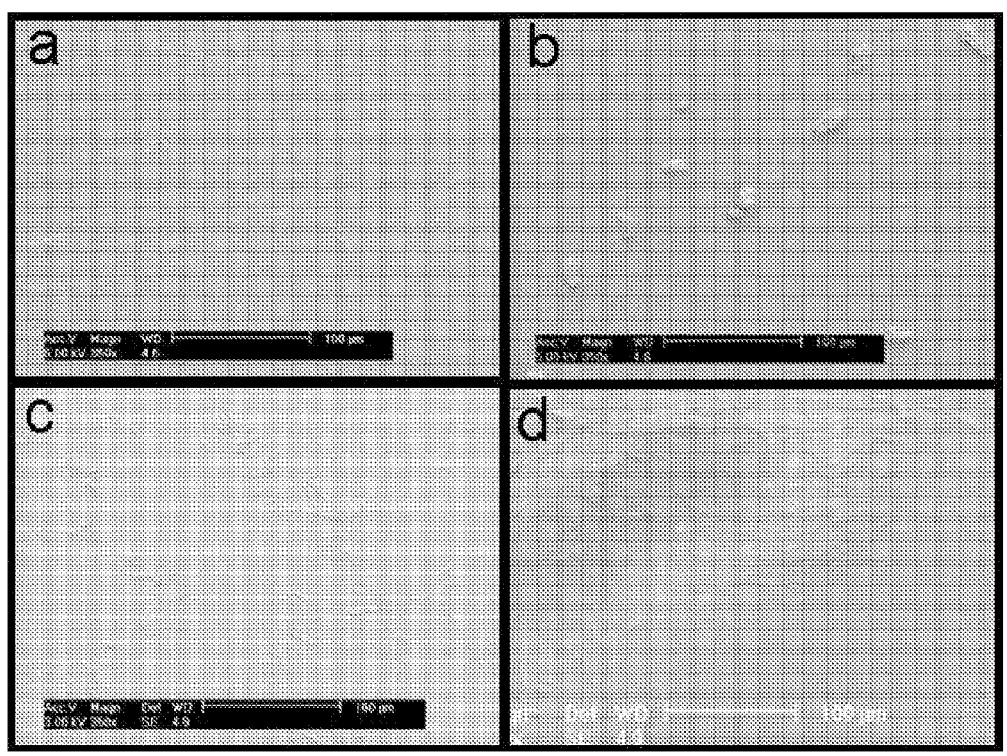
FIG. 13 shows the scanning electron micrographs (SEM) obtained by coating a mixture of angiotensin-II (1 pmol/µL) and a matrix, HCCA (α-cyano-4-hydroxycinnamic acid, 100 pmol/µL) or DHB (dihydroxybenxoic acid, 100 pmol/µL), on a MALDI plate.

FIG. 13 shows the scanning electron micrographs (SEM) obtained by coating a mixture of angiotensin-II (1 pmol/µL) and a matrix, HCCA (α-cyano-4-hydroxycinnamic acid, 100 pmol/µL) or DHB (dihydroxybenxoic acid, 100 pmol/µL), on a MALDI plate. FIG. 13a shows the MALDI sample prepared using HCCA as matrix in accordance with the present invention (scale=100 µm, the same for FIGS. 13b to 13d). FIG. 13b shows the MALDI sample prepared using HCCA as matrix in accordance with the conventional dried droplet technique. FIG. 13c shows the sample prepared using DHB as matrix in accordance with the present invention. And, FIG. 13d shows the sample prepared using DHB as matrix in accordance with the conventional dried droplet technique. The samples prepared in accordance with the present invention showed very uniform crystal growth at the surface (FIG. 13a and FIG. 13c), whereas the samples prepared by the dried droplet technique showed non-uniform crystal growth at the surface (FIG. 13b and FIG. 13d). Consequently, the samples prepared in accordance with the present invention provide uniform signals without regard to the detection site, thereby reducing analysis time and improving detection limit by 100 times or more.

Figure 14:
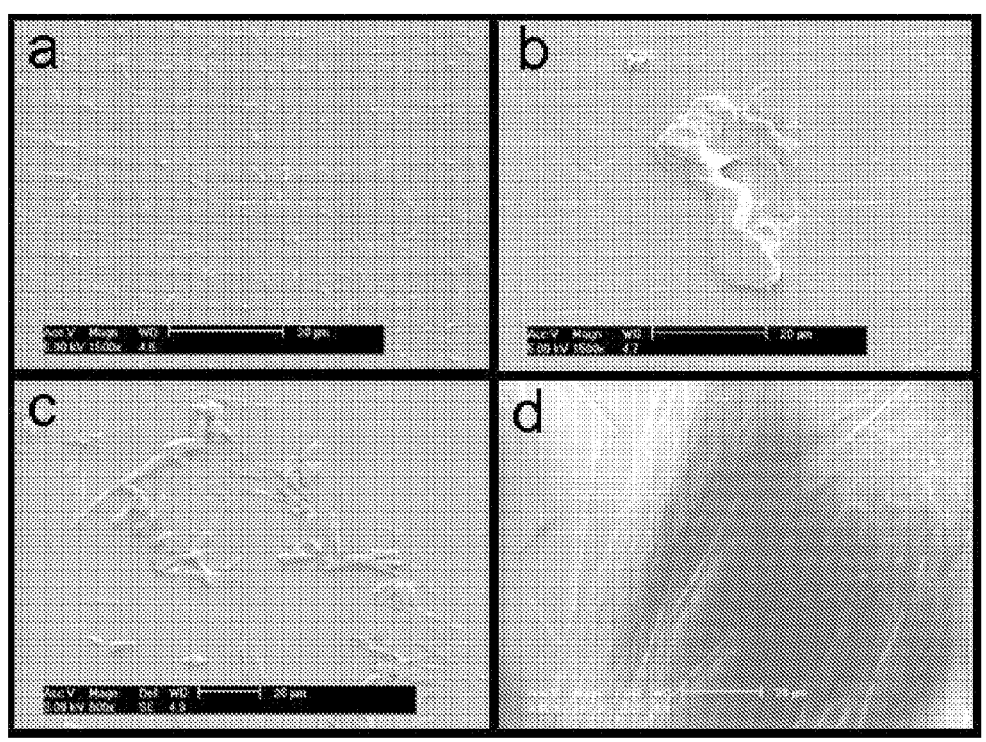
FIG. 14 shows the scanning electron micrographs obtained by coating a mixture of angiotensin-II (1 pmol/µL) and a matrix, HCCA (α-cyano-4-hydroxycinnamic acid, 100 pmol/µL) or DHB (dihydroxybenxoic acid, 100 pmol/µL), on a MALDI plate.

FIG. 14 shows the scanning electron micrographs obtained by coating a mixture of angiotensin-II (1 pmol/µL) and a matrix, HCCA (α-cyano-4-hydroxycinnamic acid, 100 pmol/µL) or DHB (dihydroxybenxoic acid, 100 pmol/µL), on a MALDI plate. FIG. 14a shows the MALDI sample prepared using HCCA as matrix in accordance with the present invention (scale=20 µm, the same for FIGS. 14b to 14d). FIG. 14b shows the MALDI sample prepared using HCCA as matrix by the conventional dried droplet technique. FIG. 14c shows the MALDI sample prepared using DHB as matrix in accordance with the present invention. And, FIG. 14d shows the MALDI sample prepared using DHB as matrix by the conventional dried droplet technique. The samples prepared in accordance with the present invention showed fine and uniform crystal particle distribution, with diameter about 2 µm (FIGS. 14a and 14c), whereas the samples prepared by the dried droplet technique showed large crystal diameter of 2 µm or larger (FIGS. 14b and 14d).

EXAMPLE 5

Figure 15:
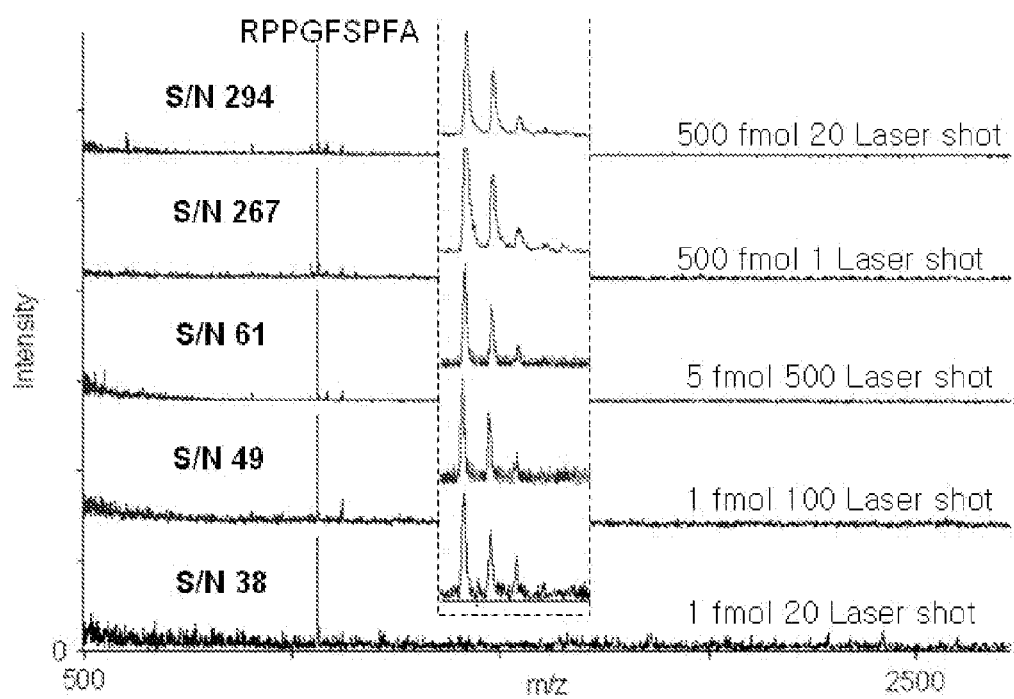
FIG. 15 shows the mass spectra obtained by preparing a sample in accordance with the present invention by injecting a mixture of bradykinin and a DHB matrix using a syringe pump and performing MALDI-TOF MS.

In order to test the detection limit of the samples prepared in accordance with the present invention, mass spectrometry was performed on bradykinin (RPPGFSPFA; SEQ ID NO: 69) and angiotensin-II (DRVYIHPF; SEQ ID NO: 70) standard samples. FIG. 15 shows the mass spectra obtained by preparing a sample in accordance with the present invention by injecting a mixture of bradykinin and a DHB matrix using a syringe pump and performing MALDI-TOF MS. FIG. 15 shows the mass spectra for 20 laser shots at a single laser spot for a 500 fmol bradykinin sample, 1 laser shot at a single laser spot for a 500 fmol bradykinin sample, 500 laser shots at a single laser spot for a 5 fmol bradykinin sample, 100 laser shots at a single laser spot for a 1 fmol bradykinin sample and 20 laser shots at a single laser spot for a 1 fmol bradykinin sample, from above to below. It can be seen that, at a concentration of 500 fmol, the mass peak of braykinin showed better signal-to-noise ratio as the laser shots were accumulated and the mass resolution was improved. Even at a low braykinin concentration of 1 fmol, a good signal-to-noise ratio of about 38 was obtained. Another important feature is that the strength of the mass peak from the matrix decreased significantly when the MALDI sample was prepared in accordance with the present invention, as compared with when the sample was prepared by the dried droplet technique. In the conventional dried droplet technique, the case where the mass peaks of the sample were hard to discern from those of the matrix was not uncommon. Since the sample/matrix crystal prepared in accordance with the present invention has a particle size about 10 times smaller than that prepared by the dried droplet technique, the quantity of ions derived from the matrix during the laser desorption ionization decreases relatively.

Figure 16:
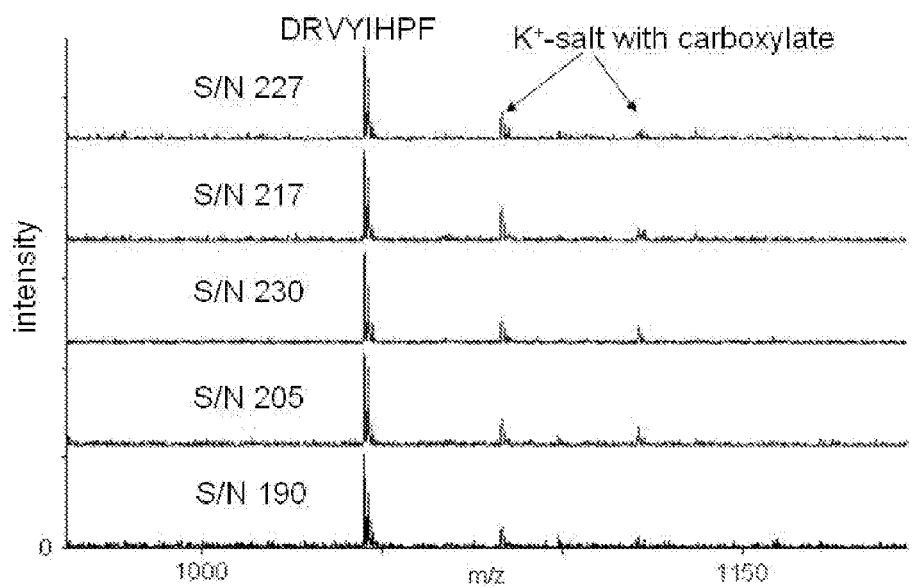
FIG. 16 shows the mass spectra obtained by preparing a MALDI sample in accordance with the present invention by passing 5 fmol angiotensin-II through a capillary LC as a standard sample and mixing it with a HCCA matrix and performing MALDI-TOF MS, where 5 laser shots were accumulated at a single laser spot.

FIG. 16 shows the mass spectra obtained by preparing a MALDI sample in accordance with the present invention by passing 5 fmol angiotensin-II through capillary LC as a standard sample and mixing it with a HCCA matrix and performing MALDI-TOF MS, where 5 laser shots were accumulated at a single laser spot. When 5 random spots were analyzed repeatedly for the same sample, the mass peaks of angiotensin-II showed quite constant signal-to-noise ratio.

EXAMPLE 6

Three standard mass spectrometry peptides—Dynorphin-a (YGGFLRRIR; SEQ ID NO: 71), angiotensin-II (DRVYIHPF; SEQ ID NO: 70) and Substance-P(RPKPQQFFGLM; SEQ ID NO: 72)—were used to detect the samples prepared in accordance with the present invention by liquid chromatography. Solutions containing each 1 pmol of the standard peptides were separated by capillary LC and mass spectrometry was performed using the MALDI sample prepared in accordance with the present invention using HCCA (100 pmol/mL) as matrix.

Figure 17:
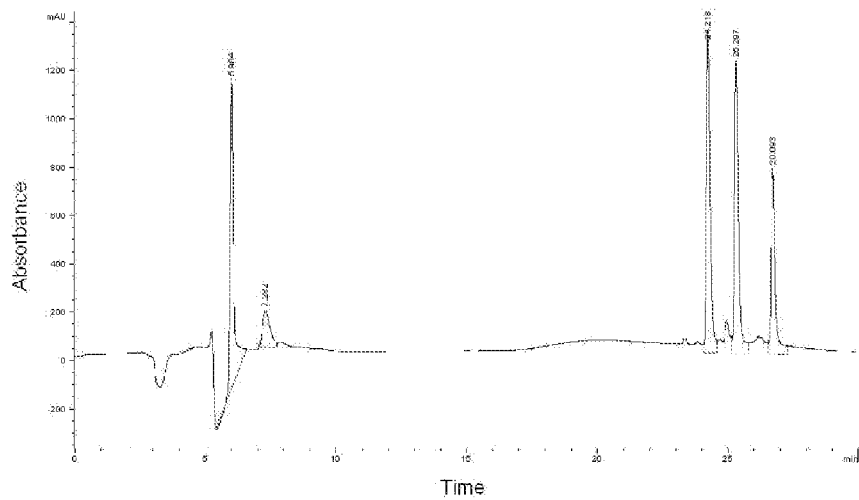
FIG. 17. shows the chromatograms obtained with a UV-Vis detector.

FIG. 17 shows the chromatograms obtained with a UV-Vis detector. It can be seen that the peptides are separated at 24 min, 25 min and 26 min.

Figure 18:
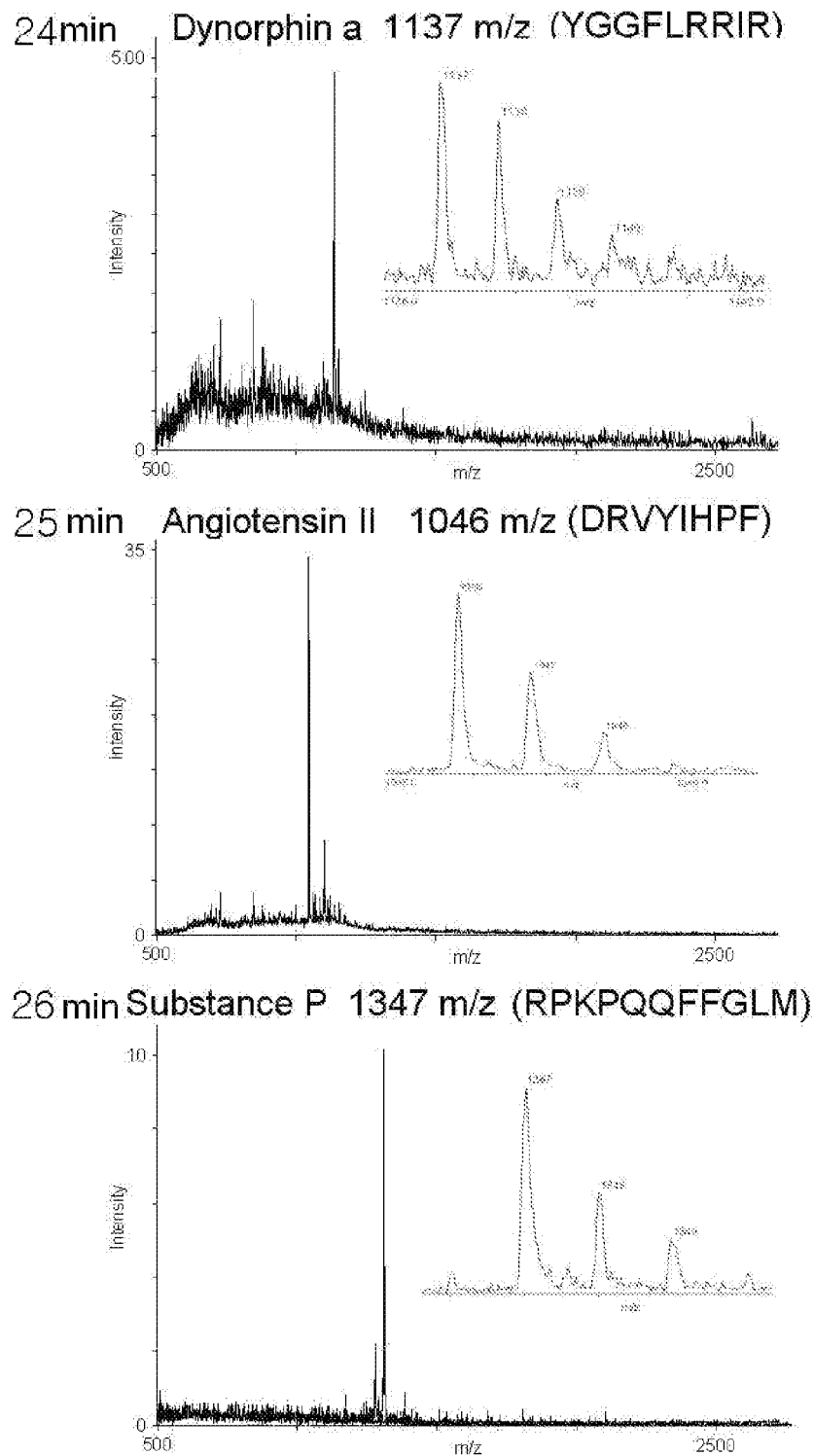
FIG. 18 shows the mass spectra obtained by performing mass spectrometry on each of the LC effluents using the MALDI samples prepared in accordance with the present invention.

FIG. 18 shows the mass spectra obtained by performing mass spectrometry on each of the LC effluents using the MALDI samples prepared in accordance with the present invention. The peptides separated at 24 min, 25 min and 26 min were identified as Dynorphin-a, angiotensin-II and Substance-P, respectively. From this, it can be seen that LC effluents can be easily separated and analyzed taking advantage of the present invention.

EXAMPLE 7

The BSA sample obtained by enzymatic cleavage with trypsin was used to test the mass detection limit concentration when the method of the present invention is coupled with LC.

Figure 19:
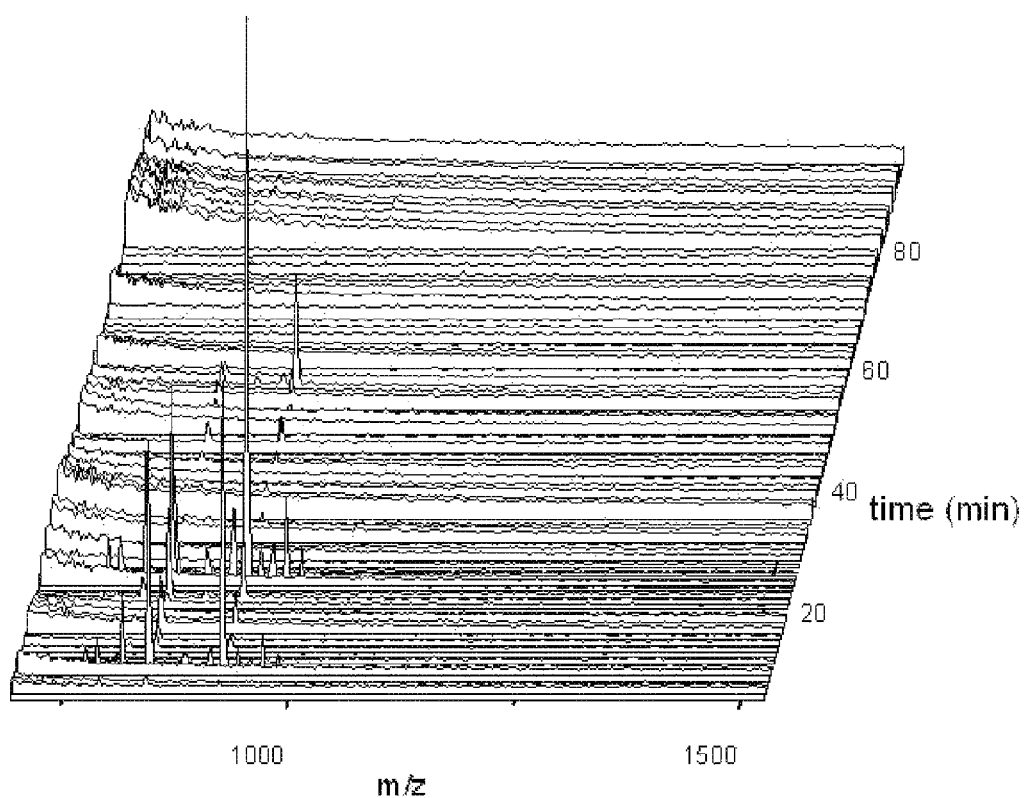
FIG. 19 shows the mass spectra obtained from a MALDI sample, which had been prepared in accordance with the present invention by separating tryptic peptides obtained by enzymatic cleavage of 100 fmol BSA with capillary LC and using DHB as matrix.
Figure 20:
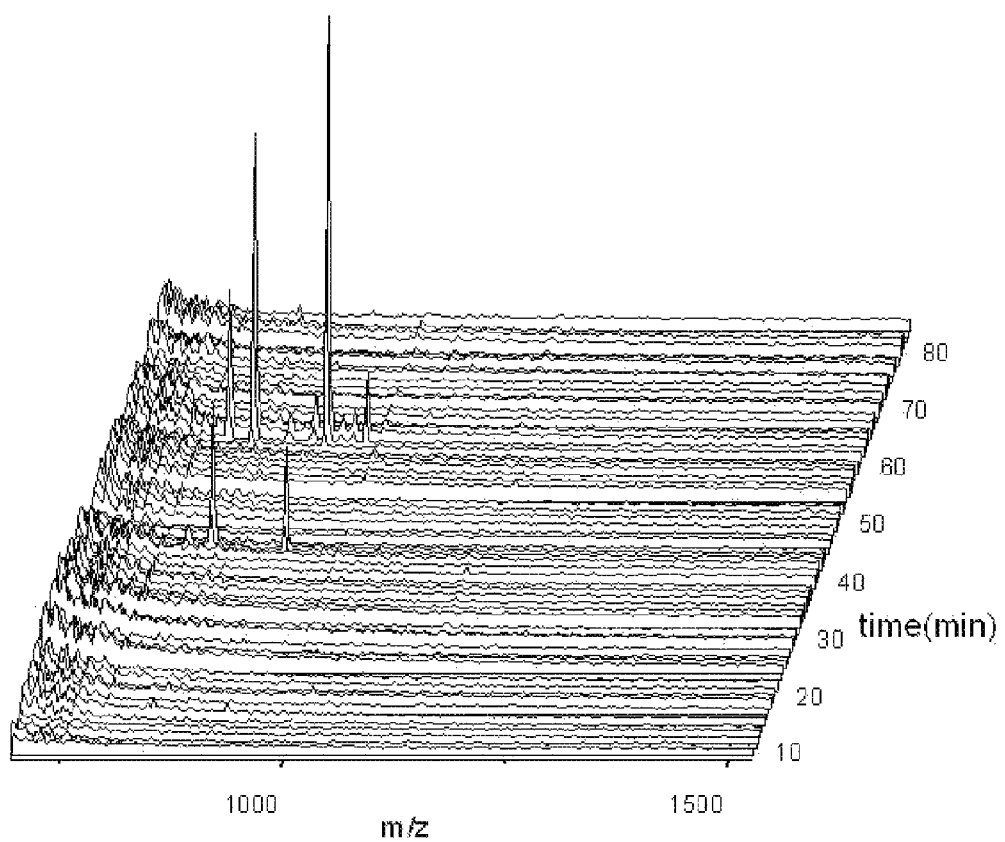
FIG. 20 shows the mass spectra of the tryptic peptides obtained by lowering the BSA concentration to 1 fmol.

FIG. 19 shows the mass spectra obtained from a MALDI sample, which had been prepared in accordance with the present invention by separating tryptic peptides obtained by enzymatic cleavage of 100 fmol BSA with capillary LC and using DHB as matrix. The mass spectra were obtained while collecting the LC effluent at the MALDI plate with one-minute interval. Laser desorption ionization was automated to obtain 5 laser shots at each single spot. The resultant mass spectrum was accumulated for 100 times. Tryptic peptides were detected for 100 fmol BSA. FIG. 20 shows the mass spectra of the tryptic peptides obtained by lowering the BSA concentration to 1 fmol. At 1 fmol concentration, 8 tryptic peptides were detected. For unknown sample, detection of about 3 tryptic peptides is considered to be positive identification, in general. Thus, detection of 8 tryptic peptides at 1 fmol concentration means that the mass detection concentration limit of the present invention is lower than 1 fmol. According to numerical calculation, the detection limit of the present invention is about 10 amol.

As apparent from the above description, the peptide sequencing method in accordance with the present invention offers improved detection sensitivity of peptides containing lysine and uniform detection of various daughter ions, because tandem mass spectrometry is performed after chemical modification. As a result, a perfect de novo peptide sequencing is possible with tandem mass spectrometry only, without database search.

The method for preparing a sample for MALDI mass spectrometry and the apparatus for the same in accordance with the present invention couple LC with MALDI-MS in order to automate the sample preparation process and an instrument for focusing electrosprayed ions in the air is used. As a result, sample/matrix crystals with very small grain size grow with uniform distribution, thereby significantly improving mass detection sensitivity and shot-to-shot S/N ratio. Consequently, noise caused by the mass peaks derived from the matrix becomes smaller and the detection sensitivity of the present invention is about 100 times or better than the conventional method.

Those skilled in the art will appreciate that the concepts and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the present invention as set forth in the appended claims.

What is claimed is:

1. A method for amino acid sequencing by MALDI (matrix-assisted laser desorption ionization) tandem mass spectrometry, which comprises the steps of:
   chemically modifying a sample peptide by esterification followed by quanidination; and
   performing mass spectrometry using a MALDI tandem mass spectrometer and a programmed de novo sequencing.

2. The method of claim 1, wherein the method further comprises a step of preparing said sample peptide by treating a sample protein with a protease prior to said chemical modification.

3. The method of claim 2, wherein said protease is trypsin, LysC or a mixture thereof.

4. The method of claim 1, wherein said guanidination is performed at lysine.

5. The method of claim 4, wherein said guanidination is performed with O-methylisourea or S-methylisourea.

6. The method of claim 1, wherein said esterification is performed at least one functional group selected from the group consisting of carboxyl group of glutamic acid, carboxyl group of aspartic acid and C-terminal carboxyl group of said peptide.

7. The method of claim 6, wherein said esterification is performed using an alcohol having 1 to 5 carbon atoms.

8. The method of claim 7, wherein at least one element selected from carbon and oxygen of said alcohol is labeled with a radioactive isotope.

9. The method of claim 1, wherein acetyl chloride or hydrochloric acid is used as catalyst in said esterification.

10. The method of claim 1, wherein said mass spectrometry using a MALDI tandem mass spectrometer comprises the steps of:
   (a) mixing a liquid sample with a matrix and electrospraying the resulting mixture to form charged sample particles;
   (b) focusing the charged particles locally with electromagnetic field using an ion-optical instrument; and
   (c) collecting the focused charged particles on a solid surface under atmospheric pressure.

* * * * *

SEQUENCE LISTING

```
<160> NUMBER OF SEQ ID NOS: 73

<210> SEQ ID NO 1
<211> LENGTH: 11
<212> TYPE: PRT
<213> ORGANISM: Bos taurus

<400> SEQUENCE: 1

His Leu Val Asp Glu Pro Gln Asn Leu Ile Lys
1               5                   10

<210> SEQ ID NO 2
<211> LENGTH: 8
<212> TYPE: PRT
<213> ORGANISM: Bos taurus

<400> SEQUENCE: 2

Ala Glu Phe Val Glu Val Thr Lys
1               5

<210> SEQ ID NO 3
<211> LENGTH: 7
<212> TYPE: PRT
<213> ORGANISM: Bos taurus

<400> SEQUENCE: 3

Tyr Leu Tyr Glu Ile Ala Arg
1               5

<210> SEQ ID NO 4
<211> LENGTH: 11
<212> TYPE: PRT
<213> ORGANISM: Bos taurus
<220> FEATURE:
<221> NAME/KEY: MISC_FEATURE
<222> LOCATION: (1)..(11)
```

```
<223> OTHER INFORMATION: /note="missequenced tryptic peptide of SEQ ID
      NO: 1"

<400> SEQUENCE: 4

His Leu Val Asp Glu Lys Pro Asn Leu Ile Lys
1               5                   10

<210> SEQ ID NO 5
<211> LENGTH: 11
<212> TYPE: PRT
<213> ORGANISM: Bos taurus
<220> FEATURE:
<221> NAME/KEY: MISC_FEATURE
<222> LOCATION: (1)..(11)
<223> OTHER INFORMATION: /note="missequenced tryptic peptide of SEQ ID
      NO. 1"

<400> SEQUENCE: 5

Tyr Ser Val Asp Glu Asn Gln Pro Leu Ile Lys
1               5                   10

<210> SEQ ID NO 6
<211> LENGTH: 8
<212> TYPE: PRT
<213> ORGANISM: Bos taurus
<220> FEATURE:
<221> NAME/KEY: MISC_FEATURE
<222> LOCATION: (1)..(8)
<223> OTHER INFORMATION: /note="missequenced tryptic peptide of SEQ ID
      NO: 2"

<400> SEQUENCE: 6

Val Thr Asp Met Glu Ala Glu Lys
1               5

<210> SEQ ID NO 7
<211> LENGTH: 10
<212> TYPE: PRT
<213> ORGANISM: Bos taurus

<400> SEQUENCE: 7

Leu Val Asn Glu Leu Thr Glu Phe Ala Lys
1               5                   10

<210> SEQ ID NO 8
<211> LENGTH: 6
<212> TYPE: PRT
<213> ORGANISM: Bos taurus

<400> SEQUENCE: 8

Phe Val Glu Val Thr Lys
1               5

<210> SEQ ID NO 9
<211> LENGTH: 7
<212> TYPE: PRT
<213> ORGANISM: Bos taurus
<220> FEATURE:
<221> NAME/KEY: MOD_RES
<222> LOCATION: (4)..(4)
<223> OTHER INFORMATION: /note="methyl-d0 esterification"
<220> FEATURE:
<221> NAME/KEY: MOD_RES
<222> LOCATION: (7)..(7)
<223> OTHER INFORMATION: /note="methyl-d0 esterification"

<400> SEQUENCE: 9

Tyr Leu Tyr Glu Leu Ala Arg
```

<210> SEQ ID NO 10
<211> LENGTH: 7
<212> TYPE: PRT
<213> ORGANISM: Bos taurus
<220> FEATURE:
<221> NAME/KEY: MOD_RES
<222> LOCATION: (4)..(4)
<223> OTHER INFORMATION: /note="methyl-d3 esterification"
<220> FEATURE:
<221> NAME/KEY: MOD_RES
<222> LOCATION: (7)..(7)
<223> OTHER INFORMATION: /note="methyl-d3 esterification"

<400> SEQUENCE: 10

Tyr Leu Tyr Glu Leu Ala Arg
1               5

<210> SEQ ID NO 11
<211> LENGTH: 7
<212> TYPE: PRT
<213> ORGANISM: Bos taurus
<220> FEATURE:
<221> NAME/KEY: MOD_RES
<222> LOCATION: (4)..(4)
<223> OTHER INFORMATION: /note="methyl-d0 esterification"
<220> FEATURE:
<221> NAME/KEY: MOD_RES
<222> LOCATION: (7)..(7)
<223> OTHER INFORMATION: /note="guanidination"

<400> SEQUENCE: 11

Tyr Leu Tyr Glu Leu Ala Lys
1               5

<210> SEQ ID NO 12
<211> LENGTH: 7
<212> TYPE: PRT
<213> ORGANISM: Bos taurus
<220> FEATURE:
<221> NAME/KEY: MOD_RES
<222> LOCATION: (4)..(4)
<223> OTHER INFORMATION: /note="methyl-d0 esterification"
<220> FEATURE:
<221> NAME/KEY: MOD_RES
<222> LOCATION: (7)..(7)
<223> OTHER INFORMATION: /note="methyl-d0 esterification"

<400> SEQUENCE: 12

Leu Tyr Tyr Glu Leu Ala Arg
1               5

<210> SEQ ID NO 13
<211> LENGTH: 7
<212> TYPE: PRT
<213> ORGANISM: Bos taurus
<220> FEATURE:
<221> NAME/KEY: MOD_RES
<222> LOCATION: (4)..(4)
<223> OTHER INFORMATION: /note="methyl-d3 esterification"
<220> FEATURE:
<221> NAME/KEY: MOD_RES
<222> LOCATION: (7)..(7)
<223> OTHER INFORMATION: /note="methyl-d3 esterification"

<400> SEQUENCE: 13

Leu Tyr Tyr Glu Leu Ala Arg
1               5

```
<210> SEQ ID NO 14
<211> LENGTH: 7
<212> TYPE: PRT
<213> ORGANISM: Bos taurus
<220> FEATURE:
<221> NAME/KEY: MOD_RES
<222> LOCATION: (4)..(4)
<223> OTHER INFORMATION: /note="methyl-d0 esterification"
<220> FEATURE:
<221> NAME/KEY: MOD_RES
<222> LOCATION: (7)..(7)
<223> OTHER INFORMATION: /note="guanidination"

<400> SEQUENCE: 14

Leu Tyr Tyr Glu Leu Ala Lys
1               5

<210> SEQ ID NO 15
<211> LENGTH: 8
<212> TYPE: PRT
<213> ORGANISM: Bos taurus
<220> FEATURE:
<221> NAME/KEY: MOD_RES
<222> LOCATION: (8)..(8)
<223> OTHER INFORMATION: /note="guanidination"

<400> SEQUENCE: 15

Val Thr Asp Met Glu Ala Glu Lys
1               5

<210> SEQ ID NO 16
<211> LENGTH: 8
<212> TYPE: PRT
<213> ORGANISM: Bos taurus
<220> FEATURE:
<221> NAME/KEY: MOD_RES
<222> LOCATION: (8)..(8)
<223> OTHER INFORMATION: /note"guanidination"

<400> SEQUENCE: 16

Ala Glu Phe Val Glu Val Thr Lys
1               5

<210> SEQ ID NO 17
<211> LENGTH: 8
<212> TYPE: PRT
<213> ORGANISM: Bos taurus
<220> FEATURE:
<221> NAME/KEY: MOD_RES
<222> LOCATION: (1)..(1)
<223> OTHER INFORMATION: /note="methyl-d0 esterification"
<220> FEATURE:
<221> NAME/KEY: MOD_RES
<222> LOCATION: (5)..(5)
<223> OTHER INFORMATION: /note="methyl-d0 esterification"
<220> FEATURE:
<221> NAME/KEY: MOD_RES
<222> LOCATION: (8)..(8)
<223> OTHER INFORMATION: /note="methyl-d0 esterification"
<220> FEATURE:
<221> NAME/KEY: MOD_RES
<222> LOCATION: (8)..(8)
<223> OTHER INFORMATION: /note="guanidination"

<400> SEQUENCE: 17

Glu Ala Phe Val Glu Val Thr Lys
1               5

<210> SEQ ID NO 18
<211> LENGTH: 8
<212> TYPE: PRT
```

```
<213> ORGANISM: Bos taurus
<220> FEATURE:
<221> NAME/KEY: MOD_RES
<222> LOCATION: (2)..(2)
<223> OTHER INFORMATION: /note="methyl-d0 esterification"
<220> FEATURE:
<221> NAME/KEY: MOD_RES
<222> LOCATION: (5)..(5)
<223> OTHER INFORMATION: /note="methyl-d0 esterification"
<220> FEATURE:
<221> NAME/KEY: MOD_RES
<222> LOCATION: (8)..(8)
<223> OTHER INFORMATION: /note="methyl-d0 esterification"
<220> FEATURE:
<221> NAME/KEY: MOD_RES
<222> LOCATION: (8)..(8)
<223> OTHER INFORMATION: /note="guanidination"

<400> SEQUENCE: 18

Ala Glu Phe Val Glu Val Thr Lys
1               5

<210> SEQ ID NO 19
<211> LENGTH: 8
<212> TYPE: PRT
<213> ORGANISM: Bos taurus
<220> FEATURE:
<221> NAME/KEY: MOD_RES
<222> LOCATION: (5)..(5)
<223> OTHER INFORMATION: /note="methyl-d0 esterification"
<220> FEATURE:
<221> NAME/KEY: MOD_RES
<222> LOCATION: (8)..(8)
<223> OTHER INFORMATION: /note="methyl-d0 esterification"
<220> FEATURE:
<221> NAME/KEY: MOD_RES
<222> LOCATION: (8)..(8)
<223> OTHER INFORMATION: /note="guanidination"

<400> SEQUENCE: 19

Val Asp Phe Val Glu Val Thr Lys
1               5

<210> SEQ ID NO 20
<211> LENGTH: 8
<212> TYPE: PRT
<213> ORGANISM: Bos taurus
<220> FEATURE:
<221> NAME/KEY: MOD_RES
<222> LOCATION: (2)..(2)
<223> OTHER INFORMATION: /note="methyl-d3 esterification"
<220> FEATURE:
<221> NAME/KEY: MOD_RES
<222> LOCATION: (5)..(5)
<223> OTHER INFORMATION: /note="methyl-d3 esterification"
<220> FEATURE:
<221> NAME/KEY: MOD_RES
<222> LOCATION: (8)..(8)
<223> OTHER INFORMATION: /note="methyl-d3 esterification"
<220> FEATURE:
<221> NAME/KEY: MOD_RES
<222> LOCATION: (8)..(8)
<223> OTHER INFORMATION: /note="guanidination"

<400> SEQUENCE: 20

Ala Glu Phe Val Glu Val Thr Lys
1               5

<210> SEQ ID NO 21
<211> LENGTH: 8
<212> TYPE: PRT
<213> ORGANISM: Bos taurus
<220> FEATURE:
```

```
<221> NAME/KEY: MOD_RES
<222> LOCATION: (1)..(1)
<223> OTHER INFORMATION: /note="methyl-d3 esterification"
<220> FEATURE:
<221> NAME/KEY: MOD_RES
<222> LOCATION: (5)..(5)
<223> OTHER INFORMATION: /note="methyl-d3 esterification"
<220> FEATURE:
<221> NAME/KEY: MOD_RES
<222> LOCATION: (8)..(8)
<223> OTHER INFORMATION: /note="methyl-d3 esterification"
<220> FEATURE:
<221> NAME/KEY: MOD_RES
<222> LOCATION: (8)..(8)
<223> OTHER INFORMATION: /note="guanidination"

<400> SEQUENCE: 21

Glu Ala Phe Val Glu Val Thr Lys
1               5

<210> SEQ ID NO 22
<211> LENGTH: 10
<212> TYPE: PRT
<213> ORGANISM: Bos taurus
<220> FEATURE:
<221> NAME/KEY: MISC_FEATURE
<222> LOCATION: (1)..(16)
<223> OTHER INFORMATION: /note="missequenced tryptic peptide of SEQ ID
      NO:46"

<400> SEQUENCE: 22

Val Leu Asn Glu Leu Thr Glu Phe Ala Lys
1               5                   10

<210> SEQ ID NO 23
<211> LENGTH: 10
<212> TYPE: PRT
<213> ORGANISM: Bos taurus
<220> FEATURE:
<221> NAME/KEY: MOD_RES
<222> LOCATION: (10)..(10)
<223> OTHER INFORMATION: /note="guanidination"

<400> SEQUENCE: 23

Val Leu Asn Glu Leu Val Met Phe Ala Lys
1               5                   10

<210> SEQ ID NO 24
<211> LENGTH: 10
<212> TYPE: PRT
<213> ORGANISM: Bos taurus
<220> FEATURE:
<221> NAME/KEY: MOD_RES
<222> LOCATION: (10)..(10)
<223> OTHER INFORMATION: /note="guanidination"

<400> SEQUENCE: 24

Val Leu Asn Glu Leu Thr Glu Phe Ala Lys
1               5                   10

<210> SEQ ID NO 25
<211> LENGTH: 10
<212> TYPE: PRT
<213> ORGANISM: Bos taurus
<220> FEATURE:
<221> NAME/KEY: MOD_RES
<222> LOCATION: (10)..(10)
<223> OTHER INFORMATION: /note="guanidination"

<400> SEQUENCE: 25
```

```
Leu Val Asn Glu Leu Thr Glu Phe Ala Lys
1               5                   10

<210> SEQ ID NO 26
<211> LENGTH: 10
<212> TYPE: PRT
<213> ORGANISM: Bos taurus
<220> FEATURE:
<221> NAME/KEY: MOD_RES
<222> LOCATION: (4)..(4)
<223> OTHER INFORMATION: /note="methyl-d0 esterification"
<220> FEATURE:
<221> NAME/KEY: MOD_RES
<222> LOCATION: (7)..(7)
<223> OTHER INFORMATION: /note="methyl-d0 esterification"
<220> FEATURE:
<221> NAME/KEY: MOD_RES
<222> LOCATION: (10)..(10)
<223> OTHER INFORMATION: /note="methyl-d0 esterification"
<220> FEATURE:
<221> NAME/KEY: MOD_RES
<222> LOCATION: (10)..(10)
<223> OTHER INFORMATION: /note="guanidination"

<400> SEQUENCE: 26

Leu Val Asn Glu Leu Thr Glu Phe Ala Lys
1               5                   10

<210> SEQ ID NO 27
<211> LENGTH: 10
<212> TYPE: PRT
<213> ORGANISM: Bos taurus
<220> FEATURE:
<221> NAME/KEY: MOD_RES
<222> LOCATION: (4)..(4)
<223> OTHER INFORMATION: /note="methyl-d0 esterification"
<220> FEATURE:
<221> NAME/KEY: MOD_RES
<222> LOCATION: (7)..(7)
<223> OTHER INFORMATION: /note="methyl-d0 esterification"
<220> FEATURE:
<221> NAME/KEY: MOD_RES
<222> LOCATION: (10)..(10)
<223> OTHER INFORMATION: /note="methyl-d0 esterification"
<220> FEATURE:
<221> NAME/KEY: MOD_RES
<222> LOCATION: (10)..(10)
<223> OTHER INFORMATION: /note="guanidination"

<400> SEQUENCE: 27

Val Leu Asn Glu Leu Thr Glu Phe Ala Lys
1               5                   10

<210> SEQ ID NO 28
<211> LENGTH: 10
<212> TYPE: PRT
<213> ORGANISM: Bos taurus
<220> FEATURE:
<221> NAME/KEY: MOD_RES
<222> LOCATION: (4)..(4)
<223> OTHER INFORMATION: /note="methyl-d3 esterification"
<220> FEATURE:
<221> NAME/KEY: MOD_RES
<222> LOCATION: (7)..(7)
<223> OTHER INFORMATION: /note="methyl-d3 esterification"
<220> FEATURE:
<221> NAME/KEY: MOD_RES
<222> LOCATION: (10)..(10)
<223> OTHER INFORMATION: /note="methyl-d3 esterification"
<220> FEATURE:
<221> NAME/KEY: MOD_RES
<222> LOCATION: (10)..(10)
<223> OTHER INFORMATION: /note="guanidination"
```

```
<400> SEQUENCE: 28

Leu Val Asn Glu Leu Thr Glu Phe Ala Lys
1               5                   10

<210> SEQ ID NO 29
<211> LENGTH: 10
<212> TYPE: PRT
<213> ORGANISM: Bos taurus
<220> FEATURE:
<221> NAME/KEY: MOD_RES
<222> LOCATION: (4)..(4)
<223> OTHER INFORMATION: /note="methyl-d3 esterification"
<220> FEATURE:
<221> NAME/KEY: MOD_RES
<222> LOCATION: (7)..(7)
<223> OTHER INFORMATION: /note="methyl-d3 esterification"
<220> FEATURE:
<221> NAME/KEY: MOD_RES
<222> LOCATION: (10)..(10)
<223> OTHER INFORMATION: /note="methyl-d3 esterification"
<220> FEATURE:
<221> NAME/KEY: MOD_RES
<222> LOCATION: (10)..(10)
<223> OTHER INFORMATION: /note="guanidination"

<400> SEQUENCE: 29

Val Leu Asn Glu Leu Thr Glu Phe Ala Lys
1               5                   10

<210> SEQ ID NO 30
<211> LENGTH: 11
<212> TYPE: PRT
<213> ORGANISM: Bos taurus

<400> SEQUENCE: 30

His Leu Val Asp Glu Lys Pro Asn Leu Leu Lys
1               5                   10

<210> SEQ ID NO 31
<211> LENGTH: 11
<212> TYPE: PRT
<213> ORGANISM: Bos taurus

<400> SEQUENCE: 31

His Leu Val Asp Glu Pro Lys Asn Leu Leu Lys
1               5                   10

<210> SEQ ID NO 32
<211> LENGTH: 11
<212> TYPE: PRT
<213> ORGANISM: Bos taurus

<400> SEQUENCE: 32

His Leu Val Asp Glu Pro Gln Asn Leu Leu Lys
1               5                   10

<210> SEQ ID NO 33
<211> LENGTH: 11
<212> TYPE: PRT
<213> ORGANISM: Bos taurus
<220> FEATURE:
<221> NAME/KEY: MOD_RES
<222> LOCATION: (11)..(11)
<223> OTHER INFORMATION: /note="guanidination"

<400> SEQUENCE: 33

Tyr Ser Val Asp Glu Asn Gln Pro Leu Leu Lys
1               5                   10
```

<210> SEQ ID NO 34
<211> LENGTH: 11
<212> TYPE: PRT
<213> ORGANISM: Bos taurus
<220> FEATURE:
<221> NAME/KEY: MOD_RES
<222> LOCATION: (11)..(11)
<223> OTHER INFORMATION: /note="guanidination"

<400> SEQUENCE: 34

Tyr Ser Val Asp Glu Glu Leu Pro Leu Leu Lys
1               5                   10

<210> SEQ ID NO 35
<211> LENGTH: 11
<212> TYPE: PRT
<213> ORGANISM: Bos taurus
<220> FEATURE:
<221> NAME/KEY: MOD_RES
<222> LOCATION: (11)..(11)
<223> OTHER INFORMATION: /note="guanidination"

<400> SEQUENCE: 35

Tyr Ser Val Asp Glu Leu Glu Pro Leu Leu Lys
1               5                   10

<210> SEQ ID NO 36
<211> LENGTH: 11
<212> TYPE: PRT
<213> ORGANISM: Bos taurus
<220> FEATURE:
<221> NAME/KEY: MOD_RES
<222> LOCATION: (4)..(4)
<223> OTHER INFORMATION: /note="methyl-d0 esterification"
<220> FEATURE:
<221> NAME/KEY: MOD_RES
<222> LOCATION: (5)..(5)
<223> OTHER INFORMATION: /note="methyl-d0 esterification"
<220> FEATURE:
<221> NAME/KEY: MOD_RES
<222> LOCATION: (11)..(11)
<223> OTHER INFORMATION: /note="methyl-d0 esterification"
<220> FEATURE:
<221> NAME/KEY: MOD_RES
<222> LOCATION: (11)..(11)
<223> OTHER INFORMATION: /note="guanidination"

<400> SEQUENCE: 36

His Leu Val Asp Glu Pro Gln Asn Leu Leu Lys
1               5                   10

<210> SEQ ID NO 37
<211> LENGTH: 11
<212> TYPE: PRT
<213> ORGANISM: Bos taurus
<220> FEATURE:
<221> NAME/KEY: MOD_RES
<222> LOCATION: (5)..(5)
<223> OTHER INFORMATION: /note="methyl-d0 esterification"
<220> FEATURE:
<221> NAME/KEY: MOD_RES
<222> LOCATION: (11)..(11)
<223> OTHER INFORMATION: /note="methyl-d0 esterification"
<220> FEATURE:
<221> NAME/KEY: MOD_RES
<222> LOCATION: (11)..(11)
<223> OTHER INFORMATION: /note="guanidination"

<400> SEQUENCE: 37

His Leu Val Glu Glu Pro Gln Asn Leu Leu Lys

-continued

```
<210> SEQ ID NO 38
<211> LENGTH: 11
<212> TYPE: PRT
<213> ORGANISM: Bos taurus
<220> FEATURE:
<221> NAME/KEY: MOD_RES
<222> LOCATION: (4)..(4)
<223> OTHER INFORMATION: /note="methyl-d0 esterification"
<220> FEATURE:
<221> NAME/KEY: MOD_RES
<222> LOCATION: (5)..(5)
<223> OTHER INFORMATION: /note="methyl-d0 esterification"
<220> FEATURE:
<221> NAME/KEY: MOD_RES
<222> LOCATION: (11)..(11)
<223> OTHER INFORMATION: /note="methyl-d0 esterification"
<220> FEATURE:
<221> NAME/KEY: MOD_RES
<222> LOCATION: (11)..(11)
<223> OTHER INFORMATION: /note="guanidination"

<400> SEQUENCE: 38

Leu His Val Asp Glu Pro Gln Asn Leu Leu Lys
1               5                   10

<210> SEQ ID NO 39
<211> LENGTH: 11
<212> TYPE: PRT
<213> ORGANISM: Bos taurus
<220> FEATURE:
<221> NAME/KEY: MOD_RES
<222> LOCATION: (5)..(5)
<223> OTHER INFORMATION: /note="methyl-d0 esterification"
<220> FEATURE:
<221> NAME/KEY: MOD_RES
<222> LOCATION: (11)..(11)
<223> OTHER INFORMATION: /note="methyl-d0 esterification"
<220> FEATURE:
<221> NAME/KEY: MOD_RES
<222> LOCATION: (11)..(11)
<223> OTHER INFORMATION: /note="guanidination"

<400> SEQUENCE: 39

Leu His Val Glu Glu Pro Gln Asn Leu Leu Lys
1               5                   10

<210> SEQ ID NO 40
<211> LENGTH: 11
<212> TYPE: PRT
<213> ORGANISM: Bos taurus
<220> FEATURE:
<221> NAME/KEY: MOD_RES
<222> LOCATION: (4)..(4)
<223> OTHER INFORMATION: /note="methyl-d3 esterification"
<220> FEATURE:
<221> NAME/KEY: MOD_RES
<222> LOCATION: (5)..(5)
<223> OTHER INFORMATION: /note="methyl-d3 esterification"
<220> FEATURE:
<221> NAME/KEY: MOD_RES
<222> LOCATION: (11)..(11)
<223> OTHER INFORMATION: /note="methyl-d3 esterification"
<220> FEATURE:
<221> NAME/KEY: MOD_RES
<222> LOCATION: (11)..(11)
<223> OTHER INFORMATION: /note="guanidination"

<400> SEQUENCE: 40

His Leu Val Asp Glu Pro Gln Asn Leu Leu Lys
1               5                   10
```

```
<210> SEQ ID NO 41
<211> LENGTH: 11
<212> TYPE: PRT
<213> ORGANISM: Bos taurus
<220> FEATURE:
<221> NAME/KEY: MOD_RES
<222> LOCATION: (4)..(4)
<223> OTHER INFORMATION: /note="methyl-d3 esterification"
<220> FEATURE:
<221> NAME/KEY: MOD_RES
<222> LOCATION: (5)..(5)
<223> OTHER INFORMATION: /note="methyl-d3 esterification"
<220> FEATURE:
<221> NAME/KEY: MOD_RES
<222> LOCATION: (11)..(11)
<223> OTHER INFORMATION: /note="methyl-d3 esterification"
<220> FEATURE:
<221> NAME/KEY: MOD_RES
<222> LOCATION: (11)..(11)
<223> OTHER INFORMATION: /note="guanidination"

<400> SEQUENCE: 41

His Leu Val Asp Glu Pro Lys Asn Leu Leu Lys
1               5                   10

<210> SEQ ID NO 42
<211> LENGTH: 7
<212> TYPE: PRT
<213> ORGANISM: Saccharomyces sp.

<400> SEQUENCE: 42

Leu Gln Asp Asp Trp Ser Lys
1               5

<210> SEQ ID NO 43
<211> LENGTH: 10
<212> TYPE: PRT
<213> ORGANISM: Saccharomyces sp.

<400> SEQUENCE: 43

Val Pro Gly Phe Gly Ser Leu Glu Glu Arg
1               5                   10

<210> SEQ ID NO 44
<211> LENGTH: 10
<212> TYPE: PRT
<213> ORGANISM: Saccharomyces sp.

<400> SEQUENCE: 44

Ala Met Ala Leu Asp Ala Gln Leu Gln Lys
1               5                   10

<210> SEQ ID NO 45
<211> LENGTH: 11
<212> TYPE: PRT
<213> ORGANISM: Saccharomyces sp.

<400> SEQUENCE: 45

Tyr Phe Asn Leu Val Thr Pro Asn Ser Pro Lys
1               5                   10

<210> SEQ ID NO 46
<211> LENGTH: 15
<212> TYPE: PRT
<213> ORGANISM: Saccharomyces sp.

<400> SEQUENCE: 46
```

```
Thr Ser Gly Ser Pro Gly Leu Gln Glu Phe Pro Glu Ala Trp Arg
1               5                   10                  15
```

```
<210> SEQ ID NO 47
<211> LENGTH: 8
<212> TYPE: PRT
<213> ORGANISM: Saccharomyces sp.
<220> FEATURE:
<221> NAME/KEY: MISC_FEATURE
<222> LOCATION: (1)..(8)
<223> OTHER INFORMATION: /note="missequenced tryptic peptide of SEQ ID
      NO:44"

<400> SEQUENCE: 47

Leu Gln Asp Asp Ala Asp Ser Lys
1               5
```

```
<210> SEQ ID NO 48
<211> LENGTH: 10
<212> TYPE: PRT
<213> ORGANISM: Saccharomyces sp.

<400> SEQUENCE: 48

Val Pro Gly Phe Gly Ser Ile Glu Glu Arg
1               5                   10
```

```
<210> SEQ ID NO 49
<211> LENGTH: 7
<212> TYPE: PRT
<213> ORGANISM: Saccharomyces sp.

<400> SEQUENCE: 49

Leu Lys Asp Asp Trp Ser Lys
1               5
```

```
<210> SEQ ID NO 50
<211> LENGTH: 10
<212> TYPE: PRT
<213> ORGANISM: Saccharomyces sp.
<220> FEATURE:
<221> NAME/KEY: MISC_FEATURE
<222> LOCATION: (1)..(10)
<223> OTHER INFORMATION: /note="missequenced tryptic peptide of SEQ ID
      NO:48"

<400> SEQUENCE: 50

Val Gly Pro Phe Gly Ser Leu Glu Glu Arg
1               5                   10
```

```
<210> SEQ ID NO 51
<211> LENGTH: 10
<212> TYPE: PRT
<213> ORGANISM: Saccharomyces sp.
<220> FEATURE:
<221> NAME/KEY: MISC_FEATURE
<222> LOCATION: (1)..(10)
<223> OTHER INFORMATION: /note="missequenced tryptic peptide of SEQ ID
      NO:48"

<400> SEQUENCE: 51

Val Pro Gly Phe Gly Ser Asn Gln Glu Arg
1               5                   10
```

```
<210> SEQ ID NO 52
<211> LENGTH: 11
<212> TYPE: PRT
<213> ORGANISM: Saccharomyces sp.
<220> FEATURE:
```

```
<221> NAME/KEY: MISC_FEATURE
<222> LOCATION: (1)..(11)
<223> OTHER INFORMATION: /note="missequenced tryptic peptide of SEQ ID
      NO:45"

<400> SEQUENCE: 52

Tyr Phe Asn Leu Val Thr Asn Pro Ser Pro Lys
1               5                   10

<210> SEQ ID NO 53
<211> LENGTH: 15
<212> TYPE: PRT
<213> ORGANISM: Saccharomyces sp.
<220> FEATURE:
<221> NAME/KEY: MISC_FEATURE
<222> LOCATION: (1)..(15)
<223> OTHER INFORMATION: /note="missequenced tryptic peptide of SEQ ID
      NO:46"

<400> SEQUENCE: 53

Thr Ser Gly Ser Gly Pro Leu Gln Glu Phe Pro Glu Ala Trp Arg
1               5                   10                  15

<210> SEQ ID NO 54
<211> LENGTH: 16
<212> TYPE: PRT
<213> ORGANISM: Saccharomyces sp.
<220> FEATURE:
<221> NAME/KEY: MISC_FEATURE
<222> LOCATION: (1)..(16)
<223> OTHER INFORMATION: /note="missequenced tryptic peptide of SEQ ID
      NO:46"

<400> SEQUENCE: 54

Thr Ser Gly Ser Pro Gly Leu Gln Glu Phe Pro Glu Ala Asp Ala Arg
1               5                   10                  15

<210> SEQ ID NO 55
<211> LENGTH: 7
<212> TYPE: PRT
<213> ORGANISM: Saccharomyces sp.
<220> FEATURE:
<221> NAME/KEY: MOD_RES
<222> LOCATION: (3)..(3)
<223> OTHER INFORMATION: /note="methyl-d3 esterification"
<220> FEATURE:
<221> NAME/KEY: MOD_RES
<222> LOCATION: (4)..(4)
<223> OTHER INFORMATION: /note="methyl-d3 esterification"
<220> FEATURE:
<221> NAME/KEY: MOD_RES
<222> LOCATION: (7)..(7)
<223> OTHER INFORMATION: /note="methyl-d3 esterification"
<220> FEATURE:
<221> NAME/KEY: MOD_RES
<222> LOCATION: (7)..(7)
<223> OTHER INFORMATION: /note="guanidination"

<400> SEQUENCE: 55

Leu Gln Asp Asp Trp Ser Lys
1               5

<210> SEQ ID NO 56
<211> LENGTH: 7
<212> TYPE: PRT
<213> ORGANISM: Saccharomyces sp.
<220> FEATURE:
<221> NAME/KEY: MOD_RES
<222> LOCATION: (3)..(3)
<223> OTHER INFORMATION: /note="methyl-d3 esterification"
<220> FEATURE:
```

-continued

```
<221> NAME/KEY: MOD_RES
<222> LOCATION: (4)..(4)
<223> OTHER INFORMATION: /note="methyl-d3 esterification"
<220> FEATURE:
<221> NAME/KEY: MOD_RES
<222> LOCATION: (7)..(7)
<223> OTHER INFORMATION: /note="methyl-d3 esterification"
<220> FEATURE:
<221> NAME/KEY: MOD_RES
<222> LOCATION: (7)..(7)
<223> OTHER INFORMATION: /note="guanidination"

<400> SEQUENCE: 56

Leu Lys Asp Asp Trp Ser Lys
1               5

<210> SEQ ID NO 57
<211> LENGTH: 8
<212> TYPE: PRT
<213> ORGANISM: Saccharomyces sp.
<220> FEATURE:
<221> NAME/KEY: MOD_RES
<222> LOCATION: (3)..(3)
<223> OTHER INFORMATION: /note="methyl-d3 esterification"
<220> FEATURE:
<221> NAME/KEY: MOD_RES
<222> LOCATION: (4)..(4)
<223> OTHER INFORMATION: /note="methyl-d3 esterification"
<220> FEATURE:
<221> NAME/KEY: MOD_RES
<222> LOCATION: (8)..(8)
<223> OTHER INFORMATION: /note="methyl-d3 esterification"
<220> FEATURE:
<221> NAME/KEY: MOD_RES
<222> LOCATION: (8)..(8)
<223> OTHER INFORMATION: /note="guanidination"

<400> SEQUENCE: 57

Leu Gln Asp Asp Asp Ala Ser Lys
1               5

<210> SEQ ID NO 58
<211> LENGTH: 10
<212> TYPE: PRT
<213> ORGANISM: Saccharomyces sp.
<220> FEATURE:
<221> NAME/KEY: MOD_RES
<222> LOCATION: (8)..(8)
<223> OTHER INFORMATION: /note="methyl-d3 esterification"
<220> FEATURE:
<221> NAME/KEY: MOD_RES
<222> LOCATION: (9)..(9)
<223> OTHER INFORMATION: /note="methyl-d3 esterification"
<220> FEATURE:
<221> NAME/KEY: MOD_RES
<222> LOCATION: (10)..(10)
<223> OTHER INFORMATION: /note="methyl-d3 esterification"

<400> SEQUENCE: 58

Val Pro Gly Phe Gly Ser Leu Glu Glu Arg
1               5                   10

<210> SEQ ID NO 59
<211> LENGTH: 10
<212> TYPE: PRT
<213> ORGANISM: Saccharomyces sp.
<220> FEATURE:
<221> NAME/KEY: MOD_RES
<222> LOCATION: (8)..(8)
<223> OTHER INFORMATION: /note="methyl-d3 esterification"
<220> FEATURE:
<221> NAME/KEY: MOD_RES
<222> LOCATION: (9)..(9)
```

```
<223> OTHER INFORMATION: /note="methyl-d3 esterification"
<220> FEATURE:
<221> NAME/KEY: MOD_RES
<222> LOCATION: (10)..(10)
<223> OTHER INFORMATION: /note="methyl-d3 esterification"

<400> SEQUENCE: 59

Val Pro Phe Gly Gly Ser Leu Glu Glu Arg
1               5                   10

<210> SEQ ID NO 60
<211> LENGTH: 10
<212> TYPE: PRT
<213> ORGANISM: Saccharomyces sp.
<220> FEATURE:
<221> NAME/KEY: MOD_RES
<222> LOCATION: (8)..(8)
<223> OTHER INFORMATION: /note="methyl-d3 esterification"
<220> FEATURE:
<221> NAME/KEY: MOD_RES
<222> LOCATION: (10)..(10)
<223> OTHER INFORMATION: /note="methyl-d3 esterification"
<220> FEATURE:
<221> NAME/KEY: MOD_RES
<222> LOCATION: (10)..(10)
<223> OTHER INFORMATION: /note="guanidination"

<400> SEQUENCE: 60

Val Pro Gly Phe Gly Ser Leu Glu Asp Lys
1               5                   10

<210> SEQ ID NO 61
<211> LENGTH: 10
<212> TYPE: PRT
<213> ORGANISM: Saccharomyces sp.
<220> FEATURE:
<221> NAME/KEY: MOD_RES
<222> LOCATION: (5)..(5)
<223> OTHER INFORMATION: /note="methyl-d3 esterification"
<220> FEATURE:
<221> NAME/KEY: MOD_RES
<222> LOCATION: (10)..(10)
<223> OTHER INFORMATION: /note="methyl-d3 esterification"
<220> FEATURE:
<221> NAME/KEY: MOD_RES
<222> LOCATION: (10)..(10)
<223> OTHER INFORMATION: /note="guanidination"

<400> SEQUENCE: 61

Met Ala Ala Leu Asp Ala Gln Leu Gln Lys
1               5                   10

<210> SEQ ID NO 62
<211> LENGTH: 10
<212> TYPE: PRT
<213> ORGANISM: Saccharomyces sp.
<220> FEATURE:
<221> NAME/KEY: MOD_RES
<222> LOCATION: (5)..(5)
<223> OTHER INFORMATION: /note="methyl-d3 esterification"
<220> FEATURE:
<221> NAME/KEY: MOD_RES
<222> LOCATION: (10)..(10)
<223> OTHER INFORMATION: /note="methyl-d3 esterification"
<220> FEATURE:
<221> NAME/KEY: MOD_RES
<222> LOCATION: (10)..(10)
<223> OTHER INFORMATION: /note="guanidination"

<400> SEQUENCE: 62

Thr Thr Ala Leu Asp Ala Gln Leu Gln Lys
1               5                   10
```

```
<210> SEQ ID NO 63
<211> LENGTH: 10
<212> TYPE: PRT
<213> ORGANISM: Saccharomyces sp.
<220> FEATURE:
<221> NAME/KEY: MOD_RES
<222> LOCATION: (5)..(5)
<223> OTHER INFORMATION: /note="methyl-d3 esterification"
<220> FEATURE:
<221> NAME/KEY: MOD_RES
<222> LOCATION: (10)..(10)
<223> OTHER INFORMATION: /note="methyl-d3 esterification"
<220> FEATURE:
<221> NAME/KEY: MOD_RES
<222> LOCATION: (10)..(10)
<223> OTHER INFORMATION: /note="guanidination"

<400> SEQUENCE: 63

Ala Met Ala Leu Asp Ala Gln Leu Gln Lys
1               5                   10

<210> SEQ ID NO 64
<211> LENGTH: 11
<212> TYPE: PRT
<213> ORGANISM: Saccharomyces sp.
<220> FEATURE:
<221> NAME/KEY: MOD_RES
<222> LOCATION: (11)..(11)
<223> OTHER INFORMATION: /note="methyl-d3 esterification"
<220> FEATURE:
<221> NAME/KEY: MOD_RES
<222> LOCATION: (11)..(11)
<223> OTHER INFORMATION: /note="guanidination"

<400> SEQUENCE: 64

Tyr Phe Asn Leu Val Thr Pro Asn Ser Pro Lys
1               5                   10

<210> SEQ ID NO 65
<211> LENGTH: 11
<212> TYPE: PRT
<213> ORGANISM: Saccharomyces sp.
<220> FEATURE:
<221> NAME/KEY: MOD_RES
<222> LOCATION: (11)..(11)
<223> OTHER INFORMATION: /note="methyl-d3 esterification"
<220> FEATURE:
<221> NAME/KEY: MOD_RES
<222> LOCATION: (11)..(11)
<223> OTHER INFORMATION: /note="guanidination"

<400> SEQUENCE: 65

Tyr Phe Gly Gly Val Thr Pro Asn Ser Pro Lys
1               5                   10

<210> SEQ ID NO 66
<211> LENGTH: 15
<212> TYPE: PRT
<213> ORGANISM: Saccharomyces sp.
<220> FEATURE:
<221> NAME/KEY: MOD_RES
<222> LOCATION: (9)..(9)
<223> OTHER INFORMATION: /note="methyl-d3 esterification"
<220> FEATURE:
<221> NAME/KEY: MOD_RES
<222> LOCATION: (12)..(12)
<223> OTHER INFORMATION: /note="methyl-d3 esterification"
<220> FEATURE:
<221> NAME/KEY: MOD_RES
<222> LOCATION: (15)..(15)
<223> OTHER INFORMATION: /note="methyl-d3 esterification"
```

```
<400> SEQUENCE: 66

Thr Ser Gly Ser Pro Gly Leu Gln Glu Phe Pro Glu Ala Trp Arg
1               5                   10                  15

<210> SEQ ID NO 67
<211> LENGTH: 15
<212> TYPE: PRT
<213> ORGANISM: Saccharomyces sp.
<220> FEATURE:
<221> NAME/KEY: MOD_RES
<222> LOCATION: (9)..(9)
<223> OTHER INFORMATION: /note="methyl-d3 esterification"
<220> FEATURE:
<221> NAME/KEY: MOD_RES
<222> LOCATION: (12)..(12)
<223> OTHER INFORMATION: /note="methyl-d3 esterification"
<220> FEATURE:
<221> NAME/KEY: MOD_RES
<222> LOCATION: (15)..(15)
<223> OTHER INFORMATION: /note="methyl-d3 esterification"

<400> SEQUENCE: 67

Thr Ser Gly Ser Pro Gly Leu Lys Glu Phe Pro Glu Ala Trp Arg
1               5                   10                  15

<210> SEQ ID NO 68
<211> LENGTH: 15
<212> TYPE: PRT
<213> ORGANISM: Saccharomyces sp.
<220> FEATURE:
<221> NAME/KEY: MOD_RES
<222> LOCATION: (9)..(9)
<223> OTHER INFORMATION: /note="methyl-d3 esterification"
<220> FEATURE:
<221> NAME/KEY: MOD_RES
<222> LOCATION: (15)..(15)
<223> OTHER INFORMATION: /note="methyl-d3 esterification"

<400> SEQUENCE: 68

Thr Ser Gly Ser Pro Gly Leu Gln Glu Phe Ser Arg Ala Trp Arg
1               5                   10                  15

<210> SEQ ID NO 69
<211> LENGTH: 9
<212> TYPE: PRT
<213> ORGANISM: Artificial
<220> FEATURE:
<223> OTHER INFORMATION: /note="Bradykinin, calbiochem Cat# 05-23-0500"

<400> SEQUENCE: 69

Arg Pro Pro Gly Phe Ser Pro Phe Arg
1               5

<210> SEQ ID NO 70
<211> LENGTH: 8
<212> TYPE: PRT
<213> ORGANISM: Homo sapiens

<400> SEQUENCE: 70

Asp Arg Val Tyr Ile His Pro Phe
1               5

<210> SEQ ID NO 71
<211> LENGTH: 9
<212> TYPE: PRT
<213> ORGANISM: Sus scrofa

<400> SEQUENCE: 71
```

```
Tyr Gly Gly Phe Leu Arg Arg Ile Arg
1               5

<210> SEQ ID NO 72
<211> LENGTH: 11
<212> TYPE: PRT
<213> ORGANISM: Artificial
<220> FEATURE:
<223> OTHER INFORMATION: /note="Substance-P, Sigma-Aldrich Cat# S6883"

<400> SEQUENCE: 72

Arg Pro Lys Pro Gln Gln Phe Phe Gly Leu Met
1               5                   10

<210> SEQ ID NO 73
<211> LENGTH: 7
<212> TYPE: PRT
<213> ORGANISM: Bos taurus
<220> FEATURE:
<221> NAME/KEY: MISC_FEATURE
<222> LOCATION: (1)..(7)
<223> OTHER INFORMATION: /note="missequenced tryptic peptide of SEQ ID
      NO: 3"

<400> SEQUENCE: 4

Leu Tyr Tyr Glu Leu Ala Arg
1               5
```